US009273140B2

(12) United States Patent
Kurosawa et al.

(10) Patent No.: US 9,273,140 B2
(45) Date of Patent: Mar. 1, 2016

(54) ANTIBODY FOR DETECTING DNA DAMAGE IN CELLS UTILIZING CELL MEMBRANE SURFACE ANTIGEN LY6D

(71) Applicants: FUJITA HEALTH UNIVERSITY, Toyoake-shi, Aichi (JP); PERSEUS PROTEOMICS INC., Tokyo (JP)

(72) Inventors: Yoshikazu Kurosawa, Toyoake (JP); Maiko Kurosawa, Toyoake (JP); Gene Kurosawa, Tokyo (JP)

(73) Assignees: FUJITA HEALTH UNIVERSITY, Toyoake-shi, Aichi (JP); Perseus Proteomics Inc., Tokyo (JP)

( * ) Notice: Subject to any disclaimer, the term of this patent is extended or adjusted under 35 U.S.C. 154(b) by 0 days.

(21) Appl. No.: 13/891,652

(22) Filed: May 10, 2013

(65) Prior Publication Data

US 2014/0004536 A1    Jan. 2, 2014

Related U.S. Application Data

(60) Provisional application No. 61/645,233, filed on May 10, 2012.

(51) Int. Cl.
| | | |
|---|---|---|
| C07K 16/30 | (2006.01) | |
| C12N 15/13 | (2006.01) | |
| C12N 15/85 | (2006.01) | |
| G01N 33/68 | (2006.01) | |
| C07K 16/28 | (2006.01) | |

(52) U.S. Cl.
CPC ............... C07K 16/30 (2013.01); C07K 16/28 (2013.01); G01N 33/6893 (2013.01); *C07K 2317/622* (2013.01)

(58) Field of Classification Search
None
See application file for complete search history.

(56) References Cited

U.S. PATENT DOCUMENTS 5,585,089 A    12/1996    Queen et al.

FOREIGN PATENT DOCUMENTS

| EP | 0 125 023 B1 | 6/1991 |
| EP | 0 120 694 B1 | 7/1993 |
| GB | 2 188 638 A | 10/1987 |
| JP | 2005-185281 A | 7/2005 |
| JP | 4870348 B2 | 2/2012 |
| WO | WO 01/62907 A1 | 8/2001 |
| WO | WO 01/96401 A1 | 12/2001 |

OTHER PUBLICATIONS

Rubinfeld (Nature Biotechnology, vol. 24, No. 2, p. 205-209, 2006).*
Lane (Nature Biotechnology, vol. 24, No. 2, p. 163-164, 2006).*
Baxevanis (Expert Opinion: Drug Discovery, vol. 3, No. 4, p. 441-452, 2008).*
Paul, Fundamental Immunology, 3rd Edition, 1993, pp. 292-295.*
Portolano, Journal of Immunology, vol. 150, p. 880-887, 1993.*
Bendig M. M. (Methods: A Companion to Methods in Enzymology, 1995; 8:83-93).*
Rudikoff et al. (Proc Natl Acad Sci USA 79: 1979-1983, 1982).*
Quak (Am. J. Pathol., 1990, 136:191-197).*
Aggelis et al., "Proteomic identification of differentially expressed plasma membrane proteins in renal cell carcinoma by stable isotope labelling of a von Hippel-Lindau transfectant cell line model," Proteomics, vol. 9, 2009, pp. 2118-2130.
Akahori et al., "Isolation of antigen/antibody complexes through organic solvent (ICOS) method," Biochemical and Biophysical Research Communications, vol. 378, 2009, pp. 832-835.
Chen et al., "Discordant Protein and mRNA Expression in Lung Adenocarcinomas*," Molecular & Cellular Proteomics 1.4, 2002, pp. 304-313.
Dowling et al., "Proteomic analysis of isolated membrane fractions from superinvasive cancer cells," Biochimica et Biophysica Acta, vol. 1774, 2007, pp. 93-101.
Fernandez-Capetillo et al., "DNA damage-induced G2-M checkpoint activation by histone H2AX and 53BP1," Nature Cell Biology, vol. 4, Dec. 2002, pp. 993-997.
Gasser et al., "The DNA damage pathway regulates innate immune system ligands of the NKG2D receptor," Nature, vol. 436, Aug. 25, 2005, pp. 1186-1190.
Hastie et al., "Combined affinity labelling and mass spectrometry analysis of differential cell surface protein expression in normal and prostate cancer cells," Oncogene, vol. 24, 2005, pp. 5905-5913.
Kurosawa et al., "Comprehensive screening for antigens overexpressed on carcinomas via isolation of human mAbs that may be therapeutic," PNAS, vol. 105, No. 20, May 20, 2008, pp. 7287-7292.
Kurosawa et al., "Methods for comprehensive indentification of membrane proteins recognized by a large number of monoclonal antibodies," Journal of Immunological Methods, vol. 351, 2009, pp. 1-12.
Ritter et al., "Serological Analysis of Human Anti-Human Antibody Responses in Colon Cancer Patients Treated with Repeated Doses of Humanized Monoclonal Antibody A33," Cancer Res, vol. 61, 2001, pp. 6851-6859.
Shiloh, "The ATM-mediated DNA-damage response: taking shape," TRENDS in Biochemical Sciences, vol. 31, No. 7, Jul. 2006, pp. 402-410.
Smirnov et al., "Genetic analysis of radiation-induced changes in human gene expresssion," Nature, vol. 459, May 28, 2009, pp. 587-591.
Zhou et al., "The DNA damage response: putting checkpoints in perspective," Nature, vol. 408, Nov. 23, 2000, pp. 433-439.

* cited by examiner

*Primary Examiner* — Mark Halvorson
*Assistant Examiner* — Michael D Allen
(74) *Attorney, Agent, or Firm* — Birch, Stewart, Kolasch & Birch, LLP

(57) ABSTRACT

To provide a method for detecting cellular DNA damage by specifically recognizing molecules responsive to DNA strand breaks. A method for detecting DNA damage in cells, which comprises administering in vivo, to cells, an antibody against a cell membrane surface antigen that is expressed in cells undergoing DNA strand breaks to a greater extent than in cells not undergoing DNA strand breaks in an environment that causes DNA damage, and analyzing the expression status of the cell membrane surface antigen.

12 Claims, 7 Drawing Sheets
(5 of 7 Drawing Sheet(s) Filed in Color)

Figure 10

```
ATGGCCGAGGTGCAGCTGGTGGAGTCTGGGGGAGGCTTGGTACAGCCTGGCAGGTCCCTG
 M  A  E  V  Q  L  V  E  S  G  G  G  L  V  Q  P  G  R  S  L

AGACTCTCCTGTGCAGCCTCTGGATTCACCTTTGATGATTATGCCATGCACTGGGTCCGG
 R  L  S  C  A  A  S  G  F  T  F  D  D  Y  A  M  H  W  V  R

CAAGCTCCAGGGAAGGGCCTGGAGTGGGTCTCAGGTATTAGTTGGAATAGTGGTAGCATA
 Q  A  P  G  K  G  L  E  W  V  S  G  I  S  W  N  S  G  S  I

GGCTATGCGGACTCTGTGAAGGGCCGATTCACCATCTCCAGAGACAACGCCAAGAACTCC
 G  Y  A  D  S  V  K  G  R  F  T  I  S  R  D  N  A  K  N  S

CTGTATCTGCAAATGAACAGTCTGAGAGCTGAGGACACGGCCTTGTATTACTGTGCAAAA
 L  Y  L  Q  M  N  S  L  R  A  E  D  T  A  L  Y  Y  C  A  K

ACGGGGATCCTCGATGCTTTTGATATCTGGGGCCAAGGGACCACGGTCACCGTCTCGAGA
 T  G  I  L  D  A  F  D  I  W  G  Q  G  T  T  V  T  V  S  R
```
```
GGCGGTGGCGGATCAGGTGGCGGTGGAAGTGGCGGTGGTGGGTCCATGGCCCAGTCTGTG    linker
 G  G  G  G  S  G  G  G  G  S  G  G  G  G  S  M  A  Q  S  V    sequence TTGACGCAGCCGCCCTCGGTGTCTGGGGCCCCCGGCAGACGGTCACCATCTCCTGCTCT
 L  T  Q  P  P  S  V  S  G  A  P  R  Q  T  V  T  I  S  C  S GGGAGCAGCTCCAACATGGACAAAATTCTGTTACCTGGTACCAGCGCCTCCCGGGTGAG
 G  S  S  S  N  I  G  Q  N  S  V  T  W  Y  Q  R  L  P  G  E GCTCCCAAACTCCTCATCTACTATGATGATCTCTTGCACTCAGGAGTCTCTGACCGATTC
 A  P  K  L  L  I  Y  Y  D  D  L  L  H  S  G  V  S  D  R  F TCTGGCTCCAAGTCTGGCACCTCAGCCTCACTGGCCATCAGTGGACTCCAGTCTGAGGAT
 S  G  S  K  S  G  T  S  A  S  L  A  I  S  G  L  Q  S  E  D GAGGCTGAGTACTACTGTGCGTCATGGGATGACAGCCTGAAAGGTCCGGTATTCGGCGGA
 E  A  E  Y  Y  C  A  S  W  D  D  S  L  K  G  P  V  F  G  G GGGACCAAACTGACCGTCCTAGGTCAGCCCAAGGCTGCCCCCTCGGTCACTCTGTTCCCG
 G  T  K  L  T  V  L  G  Q  P  K  A  A  P  S  V  T  L  F  P CCCTCCTCTGAGGAGCTTCAAGCCAACAAGGCCACACTGGTGTGTCTCATAAGTGACTTC
 P  S  S  E  E  L  Q  A  N  K  A  T  L  V  C  L  I  S  D  F TACCCGGGAGCCGTGACAGTGGCCTGGAAGGCAGATAGCAGCCCCGTCAAGGCGGGAGTG
 Y  P  G  A  V  T  V  A  W  K  A  D  S  S  P  V  K  A  G  V GAGACCACCACACCCTCCAAACAAAGCAACAACAAGTACGCGGCCAGCAGCTACCTGAGC
 E  T  T  T  P  S  K  Q  S  N  N  K  Y  A  A  S  S  Y  L  S CTGACGCCTGAGCAGTGGAAGTCCCACAAAAGCTACAGCTGCCAGGTCACGCATGAAGGG
 L  T  P  E  Q  W  K  S  H  K  S  Y  S  C  Q  V  T  H  E  G AGCACCGTGGAGAAGACAGTGGCCCCTACAGAATGTTCGGCCGC
 S  T  V  E  K  T  V  A  P  T  E  C  S  A  R
```

ANTIBODY FOR DETECTING DNA DAMAGE IN CELLS UTILIZING CELL MEMBRANE SURFACE ANTIGEN LY6D

CROSS REFERENCE TO RELATED APPLICATION

This nonprovisional application claims the benefit of U.S. Provisional Application No. 61/645,233 filed on May 10, 2012. The entire contents of the above application are hereby incorporated by reference.

TECHNICAL FIELD

The present invention relates to a method for detecting cellular DNA damage, an antibody against a cell surface antigen responsive to DNA strand breaks, and a reagent for detecting DNA damage and a pharmaceutical composition comprising the antibody.

BACKGROUND ART

It is known that DNA damage causes DNA strand breaks, although it depends on the situation. The term "DNA strand breaks" refers to a state in which hydroxyl and phosphate groups that constitute DNA have dissociated. DNA double-strand breaks are caused by external factors such as radiation and internal factors such as DNA digestion. DNA damage is known to cause various reactions, including cell cycle arrest, DNA repair, and apoptosis (Non-Patent Document 1). All of these reactions are induced by ATR and ATM kinases belonging to the PIKK family that is important for controlling the DNA damage checkpoint mechanism and DNA repair (Non-Patent Document 2). Since DNA damage leads to destruction of well-organized mechanisms of cells, many mechanisms are thought to have evolved and to have been acquired for this phenomenon. Therefore, if it would become possible to detect DNA double-strand breaks in intact living cells, it would be useful for experimental reagents, test agents, and pharmaceutical compositions. In order to realize such detection, it must be able to easily detect changes in intact target cells. The ligand (NKG2D-L) of NKG2D belonging to the C-type lectin-like receptor family is known to be expressed on the surfaces of cells undergoing DNA breaks. This suggests that cells respond to DNA damage within a range that is greater than previously expected. In particular, DNA double-strand breaks correspond to damage that causes cleavage of both strands of DNA forming a double helix structure. It is most difficult for organisms such as cancer cells to repair the damage. However, when the repair system responds to the damage to repair it, the cells can survive. In most cases, such response occurs in the nucleus and then in the cytoplasm. Changes due to such response on the cell membrane have been little known. Under such circumstances, NKG2D-L is known as a protein that is expressed on the cell membrane in response to DNA damage. The expression of this protein is induced by ATR and ATM described above and then by CHK1 and CHK2 located downstream thereof, respectively (Non-Patent Document 3).

Profiling at the mRNA level using microarrays of X-ray-irradiated cells and non-irradiated cells revealed that the expression levels of various genes change due to DNA damage (Non-Patent Document 4). It is true that many candidates of DNA damage-responsive genes were found by this method. However, it was difficult to select marker molecules that can be actually applied in practice due to a disadvantage of mismatch of the mRNA expression level and the protein expression level seen in many aspects (Non-Patent Document 5). In order to solve these problems, comprehensive analysis was carried out by incorporating proteomics technology using two-dimensional electrophoresis. In this case, by taking into account that the abundance ratio of membrane proteins is usually significantly lower than that of intracellular proteins, comprehensive analysis was also carried out by incorporating a technology of selectively labeling and concentrating membrane proteins (Non-Patent Documents 6 to 8).

First, the present inventors created a method for obtaining an antibody against a protein expressed on the cell membrane (Patent Document 1 and Non-Patent Documents 9 and 10). In addition, the present inventors succeeded in the exhaustive acquisition of cell surface antigens and suggested high usefulness and potential of the method (Non-Patent Document 11).

As a DNA damage-responsive protein molecule, a phosphorylated histone protein molecule, called γ-H2AX, is known. Histones are a group of proteins that constitute a chromosome and play a role of folding DNA which is a very long molecule in the nucleus. H2AX is a member of the histone. One of the cellular responses induced when DNA double-strand breaks occur is that H2AX becomes phosphorylated on the 139 serine position. Phosphorylated H2AX is then called "γ-H2AX." The use of a fluorescence-labeled antibody specific to γ-H2AX makes it possible to visually detect the sites of DNA double-strand breaks. γ-H2AX can be used in an environment in which reactions in the nucleus are detectable (Non-Patent Document 12).

Cancer is the leading cause of death in Japan. The number of cancer patients has been increasing each year with aging. The development of drugs and therapies with high efficacy and safety has been strongly desired. Conventional therapies such as chemotherapy and radiation are problematic because they can kill cancer cells, but at the same time, they cause damage to normal cells, resulting in induction of strong adverse reactions. To solve this problem, molecular target therapies are being actively studied, the therapies comprising designing a drug that targets a molecule specifically expressed in cancer cells and treating cancer with the drug. Among molecular targeted agents for cancer treatment, antibody drugs have been gaining a lot of attention because of their advantages, e.g., long half-life and fewer adverse reactions. Successful examples of the development of such agents include a chimeric antibody targeting CD20, called Rituxan, a humanized antibody targeting Her2/neu, called Herceptin, and a humanized antibody targeting the vascular endothelial growth factor (VEGF), called Avastin. These antibodies have been used for cancer as a target disease and the therapeutic effects have been recognized.

Antibodies used as therapeutic agents can be divided into labeled antibodies and unlabeled antibodies. It is believed that the mechanisms of unlabeled antibodies include the following: (1) antibody-dependent cellular cytotoxicity (ADCC) and complement-dependent cytotoxicity (CDC) in which immune system cells and molecules are involved; (2) inhibition of signals associated with intracellular survival and proliferation by target molecules; (3) induction of apoptosis; and (4) regulation of secretion of cytokine. Therapeutic effects can be exerted by causing the death of tumor cells or discontinuing the proliferation of tumor cells based on a combination of the above mechanisms. Labeled antibodies are obtained by linking antibodies to cytotoxic substances such as radioactive substances, toxins, enzymes, and drugs. By making use of the antibody specificity, labeled antibodies can be delivered only to cancer tissue, thereby improving the therapeutic effects and reducing the adverse reactions.

It is generally known that when a non-human animal antibody, e.g., a mouse antibody, is administered to a human, the antibody is recognized as a foreign substance so that a human antibody against the mouse antibody (Human Anti-Mouse Antibody; hereinafter referred to as "HAMA") is induced in the human body. HAMA is known to react with a mouse antibody which is administered to a human body so as to cause adverse reactions (Non-Patent Documents 13 to 16), accelerate the disappearance of the mouse antibody from the human body (Non-Patent Documents 14, 17, and 18), and reduce the therapeutic effects of the mouse antibody (Non-Patent Documents 19 and 20).

Chimeric antibodies have been developed in order to avoid such problems (Patent Documents 2 and 3). A chimeric antibody has antibody regions derived from two or more species (e.g., a variable region of a mouse antibody and a constant region of a human antibody). Accordingly, chimeric antibodies are advantageous in that features of a mouse antibody are maintained while a human complement or cytotoxic activity can be stimulated because of the presence of human Fc. However, chimeric antibodies also induce the HACA (Human Anti-Chimera Antibody) response. Moreover, recombinant antibodies characterized in that only a substituted antibody part is a recombinant antibody complementarity-determining region (i.e., "CDR") (Patent Documents 4 and 5). CDR transplant technology has been used to produce an antibody comprising a mouse CDR, a human variable region framework, and a human constant region, i.e., a "humanized antibody." However, such humanized antibody is also immunogenic to humans and causes the HAHA (Human anti-Human Antibody) reaction (Non-Patent Documents 21 and 22). Therefore, in clinical application, more safe and effective antibody drugs having no immunogenicity have been awaited.

As an aside, it can be said that acquisition of an antibody capable of recognizing an "intact" target cancer antigen present on the cell membrane surface is essential for antibody drug discovery. However, since target cancer antigens are membrane proteins, it has been difficult to obtain antibodies even against known cancer antigens. In order to solve such problem, the present inventors have created a gigantic human antibody library consisting of as many as 100 billions of independent clones and established a method of exhaustive acquisition of antibodies against proteins (cell surface antigens) present on the cell membrane surfaces of cancer cells and tissues using the library (Patent Documents 6 to 8).

PRIOR ART DOCUMENTS

Patent Documents

[Patent Document 1] JP Patent No. 4870348
[Patent Document 2] EP Patent No. 120694
[Patent Document 3] EP Patent No. 125023
[Patent Document 4] GB Patent Publication No. 2188638A
[Patent Document 5] U.S. Pat. No. 5,585,089
[Patent Document 6] WO 01/062907 pamphlet
[Patent Document 7] WO 2001/096401 pamphlet
[Patent Document 8] JP Patent Publication No. 2005-185281

Non-Patent Documents

[Non-Patent Document 1] Zhou B B S et al. Nature 408, 433-439, 2000
[Non-Patent Document 2] Shiloh Y., Trends Biochem. Sci. 31, 402-410 <2006>
[Non-Patent Document 3] Gasser S et al., Nature 436, 1186-1190 <2005>
[Non-Patent Document 4] Smirnov D A et al., Nature 459, 587-591 <2009>
[Non-Patent Document 5] Chen G et al., Mol. Cell Proteomics 1, 304-313 <2002>
[Non-Patent Document 6] Hastie C et al., Oncogene 24 5905-5913 <2005>
[Non-Patent Document 7] Dowling P et al., BBA 1774 93-101 <2007>
[Non-Patent Document 8] Aggelis V et. al., Proteomics 9, 2118-2130 <2009>
[Non-Patent Document 9] Akahori et al., BBRC 378, 832-835 <2009>
[Non-Patent Document 10] Kurosawa G et al., J. Immunol. Methods 351, 1-12 <2009>
[Non-Patent Document 11] Kurosawa G et al., Proc. Natl. Acad. Sci. USA 105, 7287-7292 <2008>
[Non-Patent Document 12] Fernandez-Capetillo O et al., Nat. Cell Biol. 12: 993-7. 2002
[Non-Patent Document 13] J. Clin. Oncol., 2, 881 (1984)
[Non-Patent Document 14] Blood, 65, 1349 (1985)
[Non-Patent Document 15] J. Natl. Cancer Inst., 80, 932 (1988)
[Non-Patent Document 16] Proc. Natl. Acad. Sci., USA, 82, 1242 (1985)
[Non-Patent Document 17] J. Nucl. Med., 26, 1011 (1985)
[Non-Patent Document 18] J. Natl. Cancer Inst., 80, 937 (1988)
[Non-Patent Document 19] J. Immunol., 135, 1530 (1985)
[Non-Patent Document 20] Cancer Res., 46, 6489 (1986)
[Non-Patent Document 21] Cancer Res. 2001; 61: 6851-6859
[Non-Patent Document 22] J Pharm Biomed Anal. 2006; 41: 1347-1353

SUMMARY OF THE INVENTION

Problems to be Resolved by the Invention

An object of the present invention is to provide a method for detecting cellular DNA damage by specifically recognizing molecules responsive to DNA strand breaks. Another object of the present invention is to provide an antibody against a cell surface antigen responsive to DNA strand breaks. A further object of the present invention is to provide a reagent for detecting DNA damage and a pharmaceutical composition comprising the antibody.

Means of Solving the Problems

As described above, an antibody targeting an antigen on the cell membrane has been developed as a reagent for detecting DNA double-strand breaks. However, it has been difficult to predict a target antigen because a phenomenon of interest occurs in the nucleus, and the antigen is presented on the membrane via a complex pathway. In addition, as a result of exhaustive analysis by proteomics technology using microarrays of cDNA or two-dimensional electrophoresis, it was difficult to develop such antibody because of the following various reasons: inconsistency in the correlation between the mRNA expression level and the protein expression level, post-translational events such as post-translational modification that occurs at the protein level, absolute lack in the proportion of the membrane protein relative to the total protein amount, and instability due to the presence of a hydrophobic region and a hydrophilic region in an identical protein. As a result of intensive studies on an original antibody production method, the present inventors have obtained a phage antibody (scFv antibody) that reacts with an antigen expressed in response to DNA double-strand breaks on the cell membrane with the applied use of the human antibody library/phage display technology. By analyzing the antibody gene sequences, the present inventors have obtained a novel amino acid sequence of the antibody including the functional CDRs. The antibody obtained by the above method is effective for detection by FACS or the like using living cells, indicating the usefulness of the antibody for a reagent for detecting DNA damage and a pharmaceutical composition. The present invention has been completed based on the above findings.

According to the present invention, there is provided a method for detecting DNA damage in cells, which comprises administering in vivo, to cells, an antibody against a cell membrane surface antigen that is expressed in cells undergoing DNA strand breaks to a greater extent than in cells not undergoing DNA strand breaks in an environment that causes DNA damage, and analyzing the expression status of the cell membrane surface antigen.

Preferably, the cell membrane surface antigen is Ly6D.
Preferably, the cells are cancer cells.
Preferably, the antibody is a human antibody.
Preferably, DNA strand breaks are caused by radiation.
Preferably, expression of Ly6D to be detected or an increase in the expression is caused by DNA double-strand break response mediated by ATM/ATR.
Preferably, expression of Ly6D to be detected or an increase in the expression is caused by DNA double-strand break response mediated by ATM/ATR with the involvement of p53.

Further, according to the present invention, there is provided an antibody that specifically reacts with human Ly6D having the amino acid sequences of SEQ ID NOS: 3, 4, and 5 as a heavy chain first complementarity-determining region (VH CDR1), a heavy chain second complementarity-determining region (VH CDR2), and a heavy chain third complementarity-determining region (VH CDR3).

Preferably, there is provided an antibody that specifically reacts with human Ly6D having: a heavy chain variable region comprising a heavy chain first complementarity-determining region of SEQ ID NO: 3 (VH CDR1), a heavy chain second complementarity-determining region of SEQ ID NO: 4 (VH CDR2), and a heavy chain third complementarity-determining region of SEQ ID NO: 5; and a light chain variable region comprising a light chain first complementarity-determining region of SEQ ID NO: 6 (VL CDR1), a light chain second complementarity-determining region of SEQ ID NO: 7 (VL CDR2), and a light chain third complementarity-determining region of SEQ ID NO: 8 (VL CDR).

Furthermore, according to the present invention, there is provided an antibody that specifically reacts with human Ly6D having an amino acid sequence derived from the amino acid sequence of any one of SEQ ID NOS: 3 to 8 by deletion, addition, substitution and/or insertion of one or more amino acids. Preferably, the activity of the antibody is equivalent to that of an antibody having the amino acid sequences of SEQ ID NOS: 3, 4, and 5 or an antibody having the amino acid sequences of SEQ ID NOS: 3 to 8.

Preferably, the antibody is a human antibody or a humanized antibody.

Preferably, the antibody is an antibody fragment selected from the group consisting of Fab, Fab', F(ab')$_2$, a single chain antibody (scFv), a dimerized V region (Diabody), a disulfide-stabilized V region(dsFv), and a peptide comprising a CDR.

In one aspect of the present invention, there is provided DNA encoding the antibody of the present invention.

In a further aspect of the present invention, there is provided a recombinant vector which comprises the DNA of the present invention.

In a yet further aspect of the present invention, there is provided a transformant obtained by introducing the recombinant vector of the present invention into a host cell.

In a yet further aspect of the present invention, there is provided a method for producing the antibody of the present invention, which comprises: culturing the transformant of the present invention in a medium; producing and accumulating the antibody of the present invention in the culture; and collecting the antibody from the culture.

In a yet further aspect of the present invention, there is provided a reagent for detecting DNA damage which comprises the antibody of the present invention.

In a yet further aspect of the present invention, there is provided a pharmaceutical composition which comprises the antibody of the present invention.

Preferably, a cytotoxic substance is bound to the antibody.
Preferably, the cytotoxic substance is a drug, toxin, or radioactive substance.
Preferably, the pharmaceutical composition of the present invention is used as an anti-cancer agent.
Preferably, cancer is solid cancer or blood cancer.

In a yet further aspect of the present invention, there is provided a method for inhibiting or treating cancer, which comprises administering the antibody of the present invention to a subject.

In a yet further aspect of the present invention, there is provided use of the antibody of the present invention for production of a reagent for detecting DNA damage, a pharmaceutical composition, or an anti-cancer agent.

Effects of the Invention

According to the present invention, there is provided an antibody capable of specifically recognizing cells in a situation in which they undergo radiation that causes DNA double-strand breaks so as to act on the cells. According to the present invention, DNA damage to cells can be detected by administering in vivo the antibody to cells and analyzing the expression status of the cell membrane surface antigen. The antibody of the present invention can be used for a reagent for detecting temporal changes in living cells undergoing DNA strand breaks and a diagnostic agent and a therapeutic agent for cancer patients subjected to radiation. Further, according to the present invention, there is provided a complete human antibody capable of specifically recognizing human Ly6D and inhibiting the survival or growth of cancer cells expressing Ly6D. When the human antibody is administered to a human, the antigenicity of the antibody is reduced and thus HAHA is not produced. Therefore, the human antibody can exhibit anti-tumor effects at high levels while causing fewer adverse reactions. That is, the anti-human Ly6D antibody of the present invention is useful as an anti-cancer agent.

BRIEF DESCRIPTION OF THE DRAWINGS

The patent or application file contains at least one color drawing. Copies of this patent or patent application publication with color drawings will be provided by the USPTO upon request and payment of the necessary fee.

FIG. 10 shows the nucleotide sequence and the amino acid sequence of the E33-139 antibody (SEQ ID NOS: 1 and 2 in the sequence listing).

EMBODIMENTS FOR CARRYING OUT THE INVENTION

Figure 1:
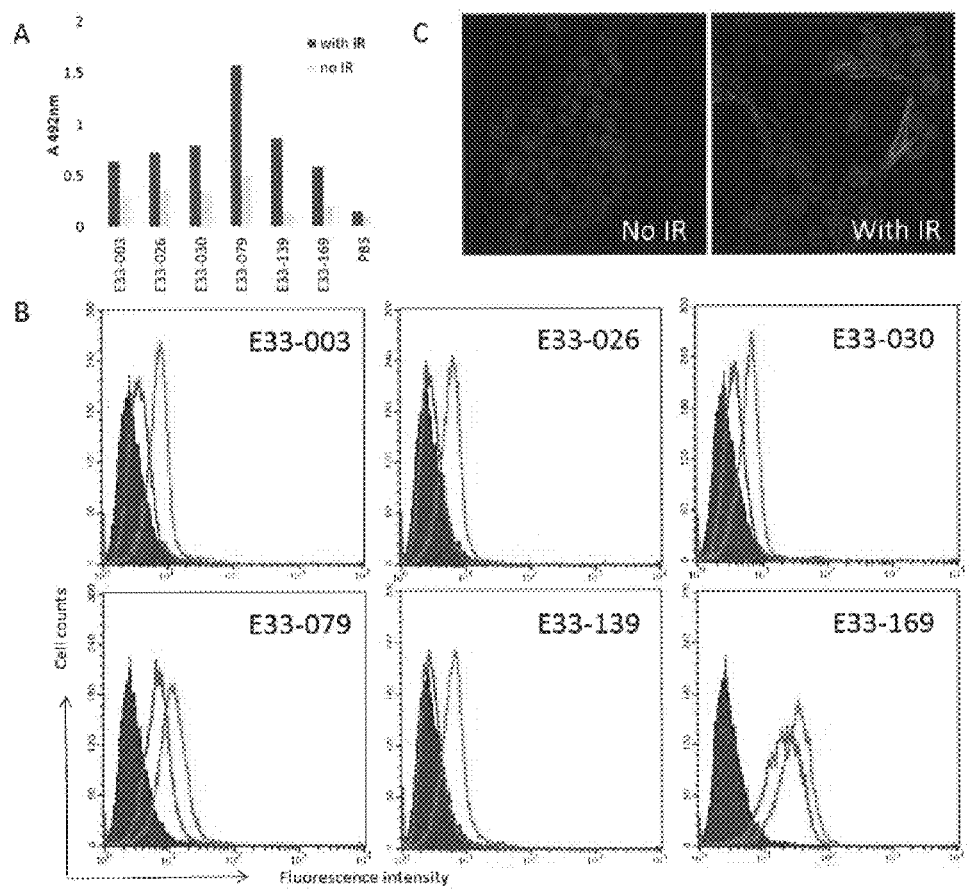
FIG. 1 shows the results of cell ELISA, FCM, and confocal laser microscopy for the selection of the E33-139 monoclonal antibody. X-ray-irradiated MCF10A cells (black bars) and non-irradiated MCF10A cells (gray bars) were subjected to ELISA using six monoclonal antibodies (A: cell ELISA). X-ray-irradiated cells (pink) and non-irradiated cells (green) were incubated with six monoclonal antibodies and subjected to FCM, and non-irradiated cells incubated with PBS were used as a negative control (purple) (B: FCM). X-ray-irradiated cells and non-irradiated cells were stained with the E33-139 monoclonal antibody (green) and DAPI (blue), respectively, and examined using a confocal laser microscope (C: immunofluorescence confocal laser microscopy).

Next, the present invention is described below in more detail.

Definition and General Technology

Scientific and technological terms used herein for the present invention include meanings generally recognized by those skilled in the art, unless otherwise specified. In general, the nomenclature system and the nomenclature technique used herein for cell and tissue culture, molecular biology, immunology, microbiology, genetics, protein and nucleic acid chemistry, and hybridization are known in the art and commonly used. The methods and techniques used in the present invention are carried out in conventional ways known in the art described in a variety of general references and more specified references cited and discussed herein, unless otherwise specified.

Ly6D

Ly6D is also called "E48 antigen" which is a GPI-anchored membrane protein with a molecular weight of approximately 15 KDa. It is known that the Ly6 gene group includes family genes such as CD59, AgE48, and TSA-1/Sca-2Ag. Most of these genes are expressed in lymphocytes, while they may be expressed in small amounts in other tissues. Among the Ly6 gene group, eight family members, including Ly6D, exist to form a cluster at human chromosome 8q24.3. Ly6D is not structurally limited. Thus, the term "human Ly6D" refers to any type of human Ly6D in the form of a monomer or polymer or in an intact form expressed on the cell membrane, a solubilized form configured in the extracellular domain, a truncated form, a mutation form obtained through gene mutation or deletion or the like, a post-translationally modified form obtained through phosphorylation, and the like.

"React" and "Reactivity"

The terms "react" and "reactivity" used herein mean the same, unless otherwise specified. Specifically, they mean that an antibody recognizes an antigen. An antigen used herein may be intact Ly6D expressed on the cell membrane or Ly6D in a truncated form or a solubilized form. Also, it may be Ly6D maintaining its conformation or denatured Ly6D. Examples of means for examining reactivity include flow cytometry (FACS), enzyme-linked immunosorbent assay (ELISA), western blot, fluorometric microvolume assay technology (FMAT), surface plasmon resonance (BIAcore), immunostaining, and immunoprecipitation.

An antibody used in flow cytometry may be an antibody labeled with a fluorescent substance such as FITC, biotin, or the like or a non-labeled antibody. A fluorescence-labeled avidin, a fluorescence-labeled anti-human immunoglobulin antibody, or the like may be used depending on the presence or absence of labeling of an antibody used or the type of the label. Reactivity can be evaluated by adding a sufficient amount of an anti-Ly6D antibody (a usual final concentration of 0.01 to 10 μg/mL) to a specimen and comparing the reactivity between the antibody and a negative control antibody or a positive control antibody.

Antibody

The following abbreviations in parentheses are used herein in a conventional manner according to need: heavy chain (H chain), light chain (L chain), heavy chain variable region (VH), light chain variable region (VL), complementarity-determining region (CDR), first complementarity-determining region (CDR1), second complementarity-determining region (CDR2), third complementarity-determining region (CDR3), heavy chain first complementarity-determining region (VH CDR1), heavy chain second complementarity-determining region (VH CDR2), heavy chain third complementarity-determining region (VH CDR3), light chain first complementarity-determining region (VL CDR1), light chain second complementarity-determining region (VL CDR2), and light chain third complementarity-determining region (VL CDR3).

The term "antibody" used herein is synonymous with immunoglobulin and it should be understood as commonly known in the art. Specifically, the term "antibody" is not limited by any particular method for producing an antibody. For example, the term "antibody" refers to, but is not limited to, a recombinant antibody, a monoclonal antibody, and a polyclonal antibody.

The term "human antibody" used herein refers to any antibody having human-derived variable region and constant region sequences. The term also refers to an antibody having a human-gene-derived sequence that has been modified to be capable of, for example, removing cysteine that can cause reduced immunogenicity, increased affinity, and undesirable folding which is considered probable. The term also refers to an antibody produced by gene recombination in non-human cells which can be subjected to glycosylation that is not particular to human cells. These antibodies can be prepared in various forms.

The term "humanized antibody" used herein refers to a non-human-derived antibody in which amino acid residues characteristic to antibody sequences of a non-human species have been substituted with amino acid residues found in the corresponding positions in a human antibody. This process of "humanization" is believed to cause reduction in immunogenicity of the obtained antibody in humans. It can be understood that a non-human-derived antibody can be humanized using techniques well known in the art. For example, the following can be referred to: Winter et al., Immunol. Today 14: 43-46 (1993). An antibody of interest can be genetically engineered by recombinant DNA techniques to substitute CH1, CH2, CH3, the hinge domain, and/or the framework domain with the corresponding human sequences. For example, the following can be referred to: WO92/02190; and U.S. Pat. Nos. 5,530,101, 5,585,089, 5,693,761, 5,693,792, 5,714,350, and 5,777,085. The term "humanized antibody" used herein also refers a chimeric human antibody and a CDR transplant antibody within the scope of its meaning.

The sequence of the framework region (FR) is not particularly limited in a variable region of the antibody of the present invention unless any substantial effect on specific binding to the corresponding antigen is observed. It is preferable to use the FR region of a human antibody. It is also possible to use the FR region of non-human animal species (e.g., rat or mouse).

The term "phage antibody" used herein refers to an scFv antibody produced by a phage. That is, it refers to an antibody fragment containing VH and VL amino acid sequences. Such fragment may contain an amino acid sequence as a tag, in addition to an amino acid as a linker.

In one embodiment, the antibody of the present invention contains a constant region, in addition to a variable region (e.g., IgG-type antibody). The sequence of a constant region is not particularly limited. For example, it is possible to use a constant region of a well-known human antibody. Any heavy-chain constant region (CH) of a human antibody can be used as long as it belongs to human immunoglobulin (hereinafter abbreviated as "hIg"). However, it preferably belongs to the hIgG class. Further, one belonging to a subclass such as hIgG1, hIgG2, hIgG3, or hIgG4 can be used. In addition, any light chain constant region (CL) can be used as long as it belongs to hIg. Further, one belonging to the κ class or the λ class may be used. It is also possible to use a constant region of a non-human animal species (e.g., mouse or rat).

As the amino acid sequence of FR or a constant region used in the antibody of the present invention, it is possible to use an unmodified amino acid sequence of FR or a constant region as the origin or a different amino acid sequence obtained from the origin by deletion, addition, substitution, and/or insertion of one or more (e.g., 1 to 8, preferably 1 to 5, more preferably 1 to 3, and particularly preferably 1 or 2) amino acids.

According to the present invention, when "the activity of an antibody is equivalent to that of the antibody of claims," it means that the antibody is equivalent to the antibody of claims in terms of the activity of binding to human Ly6D and/or anti-tumor activity. Such binding activity means ability to recognize an antigen. This antigen may be intact Ly6D expressed on the cell membrane or Ly6D in a truncated form or a solubilized form. In addition, it may be Ly6D maintaining its conformation or denatured Ly6D. For example, as a means of examining the binding activity, flow cytometry (FACS), enzyme-linked immunosorbent assay (ELISA), western blot, fluorometric microvolume assay technology (FMAT), surface plasmon resonance (BIAcore), and the like can be used.

According to the present invention, the "equivalent" activity does not necessarily mean the same level of activity. Therefore, the activity may be enhanced or reduced as long as the antibody exhibits the activity. An example of the antibody having reduced activity is an antibody having 30% or more, preferably 50% or more, more preferably 80% or more, further preferably 90% or more, and particularly preferably 95% or more of the activity of the original antibody.

The above antibody may have the amino acid sequence of a variable region (CDR sequence and/or FR sequence) modified by substitution, deletion, addition, and/or insertion of one or more amino acids as long as it has an equivalent activity of binding to Ly6D. A method for introducing a mutation into a protein known to those skilled in the art can be used as a method for preparing an amino acid sequence of an antibody having an activity of binding to Ly6D and/or anti-tumor activity by modifying the above amino acid sequence by deletion, addition, substitution, and/or insertion of one or more amino acids (e.g., 1 to 8, preferably 1 to 5, more preferably 1 to 3, and particularly preferably 1 or 2). For example, those skilled in the art would be able to prepare a mutant functionally equivalent to an antibody having the activity of binding to Ly6D by introducing an appropriate mutation into an amino acid sequence of an antibody having the activity of binding to Ly6D and/or anti-tumor activity by, for example, site-specific mutagenesis (Hashimoto-Gotoh, T, Mizuno, T, Ogasahara, Y, and Nakagawa, M. (1995), An oligodeoxyribonucleotide-directed dual amber method for site-directed mutagenesis, Gene 152, 271-275; Zoller, M. J., and Smith, M. (1983) Oligonucleotide-directed mutagenesis of DNA fragments cloned into M13 vectors, Methods Enzymol. 100, 468-500; Kramer, W, Drutsa, V, Jansen, H W, Kramer, B, Pflugfelder, M, and Fritz, H J (1984) The gapped duplex DNA approach to oligonucleotide-directed mutation construction, Nucleic Acids Res. 12, 9441-9456; Kramer W, and Fritz H J (1987) Oligonucleotide-directed construction of mutations via gapped duplex DNA Methods. Enzymol. 154, 350-367; Kunkel, T A (1985) Rapid and efficient site-specific mutagenesis without phenotypic selection, Proc. Natl. Acad. Sci. USA, 82, 488-492).

As described above, an antibody having one or more amino acid mutations in the variable region and having the activity of binding to Ly6D is also included in the antibody of the present invention.

The origin of the antibody of the present invention is not limited. Therefore, the antibody may be any animal-derived antibody such as a human antibody, a mouse antibody, or a rat antibody. In addition, it may be a chimeric antibody or a humanized antibody. In one preferred embodiment, the antibody of the present invention is a human antibody.

The antibody of the present invention may be different in terms of the amino acid sequence, molecular weight, isoelectric point, the form and the presence or absence of sugar chains, and the like depending on a cell or host that produces the antibody or a purification method. As long as the activity of the obtained antibody is equivalent to that of the antibody of the present invention, the antibody is included in the present invention. For example, an antibody having an amino acid sequence obtained by post-translational modification of an amino acid sequence described herein is also included in the present invention. Further, an antibody having an amino acid sequence obtained by post-translational modification of amino acids other than known amino acids subjected to post-translational modification is included in the present invention as long as it has the activity comparable to that of the antibody of the present invention. Moreover, if the antibody of the present invention is expressed in a prokaryotic cell such as *Escherichia coli*, a methionine residue is added to the N-terminus of the amino acid sequence of the original antibody. Such antibody is also included in the antibody of the present invention. An antibody having an amino acid sequence obtained by post-translational modification of amino acids other than known amino acids subjected to post-translational modification is included in the present invention as long as it has the activity comparable to that of the antibody of the present invention.

Preparation of an Antibody (1) ScFv that Reacts with the Antigen by a Phage Display Library The antibody of the present invention can be prepared according to methods known in the art. For example, a library including a repertoire of antibodies having various levels of affinity to Ly6D can be provided using phage display technology. Then, an antibody against Ly6D can be identified and isolated by screening the library. Preferably, the phage library is an scFv phage display library generated using human VL and VH cDNAs prepared from mRNA isolated from human B cells. A method for preparing and screening such library is known in the art. Genetic material is collected from phage clones showing reactivity obtained by screening using human Ly6d as an antigen. The gene of the selected phage is analyzed to determine the DNA sequences of VH and VL encoding a variable region of a human antibody that binds to the antigen. A human antibody can be obtained by converting scFv into IgG using the sequence of scFv.

(2) Conversion of scFv into IgG (Preparation of a Human Antibody)

A human antibody is obtained by preparing an H- or L-chain expression vector, causing the vector to be expressed in a host cell, and collecting/purifying the secreted supernatant. Alternatively, a human antibody can be obtained by causing expression of VH and VL by the same vector (tandem type). These methods are known in the art and the following can be referred to: WO92/01047, WO92/20791, WO93/06213, WO93/11236, WO93/19172, WO95/01438, WO95/15388, and WO97/10354.

Specifically, a full-length heavy chain gene can be obtained by ligating DNA encoding VH to a different DNA molecule encoding a heavy chain constant region (composed of CH1, CH2, and CH3). The sequence of the human heavy chain constant region gene has been known in the art (e.g., Kabat, E. A. et al., (1991), Sequences of Proteins of Immunological Interest, Fifth Edition, U.S. Department of Health and Human Services, NIH Publication, No. 91-3242). A DNA fragment including these regions can be obtained by standard PCR amplification. The heavy chain constant region may be a constant region of IgG1, IgG2, IgG3, IgG4, IgA, IgE, IgM, or IgD and most preferably IgG1 or IgG2. The IgG1 constant region sequence may be a sequence of any one of various alleles such as Gm (1), Gm (2), Gm (3), and Gm (17) known to be produced among different individuals or an allotype thereof. Such allotype corresponds to a naturally occurring amino acid substitution in the IgG1 constant region.

A full-length L-chain gene (and the Fab light chain gene) can be obtained by ligating DNA encoding VL to a different DNA molecule encoding the light chain constant region (CL). The sequence of the human light chain constant region has been known in the art (e.g., Kabat, E. A. et al., (1991), Sequences of Proteins of Immunological Interest, Fifth Edition, U.S. Department of Health and Human Services, NIH Publication, No. 91-3242). A DNA fragment including these regions can be obtained by standard PCR amplification. The light chain constant region may be the κ or λ constant region. The κ constant region may be any one of various alleles such as Inv (1), Inv (2), or Inv (3) known to be produced among different individuals. The λ constant region may be derived from one of three λ genes An H- or L-chain expression vector is prepared by inserting DNA encoding the H or L chain obtained as described above into an expression vector. A human antibody is obtained by causing the vector to be expressed in a host cell and collecting/purifying the secreted supernatant. Examples of an expression vector include plasmid, retrovirus, adenovirus, adeno-associated virus (AAV), plant viruses such as cauliflower mosaic virus or tobacco mosaic virus, cosmid, YAC, and EBV-derived episome. An expression vector and an expression control sequence are selected in correspondence with a host cell to be used for expression. The antibody light chain gene and the antibody heavy chain gene may be separately inserted into different vectors or they may be inserted into the same expression vector. The antibody gene is inserted into an expression vector by a standard method (e.g., ligation of a complementary restriction site on an antibody gene fragment or a blunt end (if there is no restriction site) with a vector).

Preferably, a vector encodes a functionally complete human CH or CL immunoglobulin sequence having an appropriate restriction site that has been genetically engineered in such a manner that any VH or VL sequence can be readily inserted into the vector so as to be expressed therein as described above. In such vector, splicing usually takes place between the splice donor site in the inserted J region and the splice acceptor site preceding the human C domain and even in the splice region present in the human CH exon. Polyadenylation and transcription termination take place at naturally occurring chromosomal sites located downstream of the coding region. Further, it is also possible for a recombinant expression vector to encode a signal peptide that facilitates secretion of a host cell-derived antibody chain. The antibody chain gene can be cloned into a vector such that a signal peptide is ligated in-frame to the amino end of an immunoglobulin chain. The signal peptide may be an immunoglobulin signal peptide or a heterologous signal peptide (i.e., a peptide from a non-immunoglobulin protein).

The expression vector of the antibody of the present invention may have additional sequences such as a sequence capable of controlling replication of a vector in a host cell (e.g., a sequence of the replication origin) and a selection marker gene, in addition to the antibody gene and a control sequence. The selection marker gene facilitates the selection of a host cell to which a vector has been introduced. For example, in general, the selection marker gene imparts resistance against drugs such as G418, hygromycin, and methotrexate on a host cell into which a vector has been introduced. Preferable examples of selection marker genes include the dihydrofolate reductase (DHFR) gene (used with methotrexate selection/amplification in a dhfr-host cell), the neomycin phosphotransferase gene (G418 selection), and the glutamate synthetase gene.

A host cell is transformed by an antibody gene expression vector produced by the above method. Any cell such as a bacterium, yeast, an animal cell, an insect cell, or a plant cell can be used as a host as long as it can produce the antibody of the present invention. Preferably, a host cell is an animal cell. Examples of animal cells include Chinese hamster ovary cells (CHO/dhfr(−) cells and CHO/DG44 cells), monkey-derived cells (COS cells) (A. Wright & S. L. Morrison, J. Immunol. 160, 3393-3402 (1998)), and SP2/0 cells (mouse myeloma) (K. Motmans et al., Eur. J. Cancer Prev. 5, 512-5199 (1996), R. P. Junghans et al., Cancer Res. 50, 1495-1502 (1990)). For transformation, a lipofectin method (R. W. Malone et al., Proc. Natl. Acad. Sci. USA 86, 6007 (1989); P. L. Felgner et al., Proc. Natl. Acad. Sci. USA 84, 7413 (1987)), an electroporation method, a calcium phosphate method (F. L. Graham & A. J. van der Eb, Virology 52, 456-467 (1973)), and a DEAE-Dextran method are preferably used.

After the culture of the transformant, a human antibody is separated and purified from the cells of the transformant or the culture liquid. For the separation and purification of the antibody, techniques such as centrifugation, ammonium sulfate fractionation, salting out, ultrafiltration, affinity chromatography, ion exchange chromatography, and gel filtration chromatography can be used in combination according to need.

Antibody Fragment

An antibody fragment can be prepared based on the antibody of the present invention or the sequence information of the gene encoding the antibody of the present invention. Examples of an antibody fragment include Fab, Fab', F(ab')$_2$, scFv, and dsFv antibody fragments.

Fab is obtained by digesting IgG with papain in the presence of cysteine. Fab is a fragment with a molecular weight of about 50,000 which is composed of H-chain and L-chain variable regions and an H-chain fragment consisting of the CH1 domain and a part of the hinge region. In the present invention, Fab can be obtained by digesting the above antibody with papain. It is also possible to prepare Fab from a transformant obtained by incorporating DNA encoding a part of the H chain and the L chain of the antibody into an appropriate vector and carrying out transformation using the vector.

Fab' is a fragment with a molecular weight of about 50,000 obtained by cleaving a disulfide bond between H chains of F(ab')$_2$ described below. In the present invention, Fab' is obtained by digesting the above antibody with pepsin and cleaving the disulfide bond with a reducing agent. In addition, as in the case of Fab, Fab' can be prepared by a gene engineering technique using DNA encoding Fab'.

F(ab')$_2$ is obtained by digesting IgG with pepsin. F(ab')$_2$ is a fragment with a molecular weight of approximately 100,000 which is formed with Fab' fragments that are bound to each other via disulfide bonds. Each Fab' fragment is composed of L-chain and H-chain variable regions and an H-chain fragment consisting of the CH1 domain and a part of the hinge region. In the present invention, F(ab')$_2$ can be obtained by digesting the above antibody with pepsin. In addition, as in the case of Fab, F(ab')$_2$ can be prepared by a gene engineering technique using DNA encoding F(ab')$_2$.

scFv is an antibody fragment obtained by linking the C terminus of one of the H chain and the L chain of Fv consisting of an H-chain variable region and an L-chain variable region to the N terminus of the other chain using an appropriate peptide linker to form a linear chain. As a peptide linker, for example, highly flexible (GGGGS)$_3$ (SEQ ID NO:

9) can be used. For example, DNA encoding an scFv antibody is constructed using DNA encoding the H-chain variable region and the L-chain variable region of the above antibody and DNA encoding a peptide linker, the DNA is incorporated into an appropriate vector, and a transformant is obtained by transformation using the vector. scFv can be prepared from the resulting transformant.

dsFv is a Fv fragment obtained by introducing a Cys residue at an appropriate site of each of the H-chain variable region and the L-chain variable region and stabilizing the H-chain variable region and the L-chain variable region by disulfide bonding. The site of each chain at which a Cys residue is introduced can be determined based on the conformation predicted by molecular remodeling. In the present invention, for example, the conformation is predicted based on the amino acid sequences of the H-chain and L-chain variable regions of the antibody, DNAs encoding the H-chain variable region and the L-chain variable region into each of which a mutation has been introduced are constructed based on the prediction, the DNAs are incorporated into an appropriate vector, and a transformant is obtained by transformation using the vector. dsFv can be prepared from the resulting transformant.

It is also possible to multimerize an antibody fragment by ligating scFv antibody, dcFv antibody or the like using an appropriate linker or by fusing an antibody fragment with streptavidin.

Method and Reagent for Detecting DNA Damage

According to the present invention, DNA damage to cells can be detected by administering in vivo, to cells, an antibody against a cell membrane surface antigen, the cell membrane surface antigen being expressed in cells undergoing DNA strand breaks to a greater extent than in cells not undergoing DNA strand breaks in an environment that cause DNA damage, and analyzing the expression status of the cell membrane surface antigen. Examples of cells undergoing DNA strand breaks in an environment that cause DNA damage include cells undergoing DNA strand breaks due to radiation. The type of such cells may be, but is not limited to, cancer cells. A cell membrane surface antigen is not particularly limited as long as it is expressed in cells undergoing DNA strand breaks to a greater extent than in cells not undergoing DNA strand breaks in an environment that cause DNA damage. An example of such cell membrane surface antigen is Ly6D. That is, the antibody against Ly6D of the present invention described above is useful as a reagent for detecting DNA damage.

Pharmaceutical Composition

According to the present invention, a pharmaceutical composition comprising the antibody of the present invention is provided. One embodiment of the present invention relates to, but is not limited to, treatment of cancer. A non-cancer disease for which high expression of Ly6D is observed also falls within the scope of the present invention. In a further preferable embodiment, examples of cancer include solid cancer (e.g., lung cancer, colon cancer, stomach cancer, bladder cancer, pancreatic cancer, prostate cancer, liver cancer, cervical cancer, uterine cancer, ovarian cancer, breast cancer, head and neck cancer, or skin cancer) and blood cancer (e.g., leukemia, lymphoma, or myeloma).

In one embodiment, the antibody of the present invention is used as an active ingredient of the pharmaceutical composition of the present invention. Anti-tumor effects can be exerted by making use of cytostatic activity, cell death induction activity, ADCC activity, CDC activity, and the like of the antibody. The antibody may have one of such activities or simultaneously have a plurality of them. That is, a naked antibody is an active ingredient of the pharmaceutical composition.

In another embodiment, the antibody of the present invention can be used as a cancer treatment agent in a missile therapy for specifically targeting cancer tissues. Specifically, the missile therapy is intended to promote treatment effects and alleviate adverse reactions by administering an antibody bound to a substance that causes damage to cancer cells so as to allow the substance to be transferred specifically to cancer sites.

Examples of a substance that causes damage to cancer cells include cytotoxic substances such as drugs, toxins, and radioactive materials. The antibody can be bound to a cytotoxic substance by a method known to those skilled in the art (Clin Cancer Res. 2004 Jul. 1; 10(13): 4538-49).

As a drug that is bound to the antibody, a known substance that causes damage to cancer cells can be used. Examples of such drug include, but are not limited to, duocarmycin, analogs and inducers of duocarmycin, CC-1065, duocarmycin analogs mainly composed of CBI, duocarmycin analogs mainly composed of MCBI, duocarmycin analogs mainly composed of CCBI, doxorubicin, doxorubicin conjugate, morpholino-doxorubicin, cyano-morpholino-doxorubicin, dolastatin, dolestatin-10, combretastatin, calicheamicin, maytansine, maytansine analogs, DM1, DM2, DM3, DM4, DMI, auristatin E, auristatin EB (AEB), auristatin EFP (AEFP), monomethyl auristatin E (MMAE), monomethyl auristatin F (MMAF), 5-benzoylvaleric acid-AE ester (AEVB), tubulysin, disorazole, epothilone, paclitaxel, docetaxel, SN-38, topotecan, rhizoxin, echinomycin, colchicine, vinblastine, vindesine, estramustine, cemadotin, eleutherobin, methotrexate, methopterin, dichloromethotrexate, 5-fluorouracil, 6-mercaptopurine, cytosine arabinoside, melphalan, leurosine, leurosidine, actinomycin, daunorubicin, daunorubicin conjugate, mitomycin C, mitomycin A, caminomycin, aminopterin, tallysomycin, podophyllotoxin, podophyllotoxin derivatives, etoposide, etoposide phosphate, vincristine, taxol, taxotere retinoic acid, butyric acid, $N^8$-acetyl spermidine, and camptothecin.

The binding between a drug and an antibody may be direct binding via linking groups thereof or indirect binding via a linker or a different substance.

As a linking group for direct binding between a drug and an antibody, disulfide bond using SH group, a bond via maleimide and the like can be used. For example, an intramolecular disulfide bond of the Fc region of an antibody and a disulfide bond of a drug are reduced such that they are bound to each other by a disulfide bond. In another method, they are bound to each other by a maleimide bond. In another method, cysteine is introduced into an antibody by a gene engineering technique.

It is also possible to indirectly bind an antibody and a drug via a different substance (linker). It is desirable for a linker to have one or more types of functional groups which react with an antibody and/or a drug. Examples of functional groups include amino groups, carboxyl groups, mercapto groups, maleimide groups, and pyridinyl groups.

Examples of a linker include, but are not limited to, N-succinimidyl-4-(maleimidemethyl)cyclohexanecarboxylate (SMCC), N-succinimidyl-4-(N-maleimidemethyl)-cyclohexane-1-carboxy-(6-amidocaproate) (LC-SMCC), κ-maleimide undecanoic acid-N-succinimidyl ester (KMUA), γ-maleimide butyric acid N-succinimidyl ester (GMBS), ε-maleimide caproic acid N-hydroxysuccinimide ester (EMCS), m-maleimide-benzoyl-N-hydroxysuccinimide ester (MBS), N-(α-maleimide acetoxy)-succinimide ester (AMAS), succinimidyl-6-(β-male imide propionamide) hexanoate (SMPH), N-succinimidyl-4-(p-maleimide phenyl)-butyrate (SMPB), N-(p-maleimide phenyl) isocyanate (PMPI), 6-maleimide caproyl (MC), maleimide propanoyl (MP), p-aminobenzyloxy carbonyl (PAB), N-succinimidyl-4-(2-pyridyldithio)pentanoate (SPP), and N-succinimidyl(4-iodo-acetyl) aminobenzoic acid ester (SIAB). For example, the linker may be a peptide linker such as valine-citrulline (Val-Cit) or alanine-phenylalanine (ala-phe). Alternatively, the above examples of the linker may be appropriately used in combination.

A method for binding an antibody and a drug can be carried out in accordance with, for example, the method described in the following: Cancer Research, 68(22) 9280 (2008); Nature Biotechnology, 26(8) 925 (2008); Bio Conjugate Chemistry, 19, 1673 (2008); Cancer Research, 68(15) 6300 (2008); or JP 2008-516896.

An example of a toxin is a so-called immunotoxin obtained by binding a toxin to an antibody by a chemical or gene engineering technique. Examples thereof include diphtheria toxin A chain, *Pseudomonas* endotoxin, lysine chain, deglicosylated ricin A chain (Gelonin or Saporin).

As a radioactive material to be used, it is possible to use a material known to those skilled in the art. Examples thereof include yttrium-90 ($^{90}$Y), rhenium-186 ($^{186}$Re), rhenium-188 ($^{188}$Re), copper-67 ($^{67}$Cu), iron-59 ($^{59}$Fe), strontium-89 ($^{89}$Sr), gold-198 ($^{198}$Au), mercury-203 ($^{203}$Hg), lead-212 ($^{212}$Pb), dysprosium-165 ($^{165}$Dy), ruthenium-103 ($^{103}$Ru), bismuth-212 ($^{212}$Bi), bismuth-213 ($^{213}$Bi), holmium-166 ($^{166}$Ho), samarium-153 ($^{153}$Sm), and lutetium-177 ($^{177}$Lu). Preferably, $^{90}$Y, $^{153}$Sm, and $^{177}$Lu can be used.

Binding of a radioactive material and an antibody can be carried out by a method known to those skilled in the art (Bioconjug Chem. 1994 March-April; 5(2): 101-4).

Cancer treatment using an antibody to which a compound containing a radioactive isotope has been bound can be carried out by a method known in the art (Bioconjug Chem 1998 November-December; 9(6): 773-82). Specifically, at first, a small amount of an antibody to which a compound containing a radioactive isotope has been bound is administered to a patient and the patient undergoes whole-body scintigraphy. If it is confirmed that the amount of the antibody bound to cells in normal tissues is small and the amount of the antibody bound to cancer cells is large, a large amount of the antibody to which a compound containing a radioactive isotope has been bound can be administered.

A preparation formulated with a pharmaceutical composition containing the anti-human Ly6D antibody of the present invention is also included within the scope of the present invention. Preferably, such preparation contains a pharmaceutically acceptable diluent or carrier, in addition to the pharmaceutical composition containing the antibody. Alternatively, it may be a mixture containing a different antibody or a different drug such as an anti-cancer agent. Examples of a suitable carrier include, but are not limited to, physiological saline, phosphate buffered saline, phosphate buffered saline glucose solution, and buffered saline. Alternatively, the antibody may be freeze-dried such that it can be used by reconstituting the antibody with the addition of an aqueous buffer solution described above at the time of need. Examples of a dosage form include: tablets, capsules, granules, powders, syrups, and the like for oral administration; injections (e.g., subcutaneous, intravenous, intramuscular, and intraperitoneal injections); and agents for parenteral administration such as agents for transdermal, transmucosal, transnasal, or transpulmonary administration and suppositories. The pharmaceutical composition of the present invention may be administered alone or in combination with other drugs.

The dose of the pharmaceutical composition of the present invention would vary depending on symptoms, age, weight, etc. In general, the amount of the antibody for an adult per day is about 0.01 mg to 1000 mg for oral administration. The daily dosage of the antibody can be administered once or in several portions. For parenteral administration, the antibody can be administered at a dose (per administration) of approximately 0.01 mg to 1000 mg by subcutaneous injection, intramuscular injection or intravenous injection.

The present invention will be described in more detail with reference to the Examples below; however, the present invention is not limited by the Examples.

EXAMPLES

Experimental Materials and Methods (1) Cells, Antibodies, and an Antibody Library The MCF10A cell line was provided by Dr. T. Ohta, St. Marianna University, Japan, and the FaDu and A431 cell lines were purchased from ATCC. Mouse anti-human LY6DAb and Mouse anti-human GML were purchased from Abnova Corp. The AIMS5 antibody library has been previously reported (Morino et al., 2001 *J. Immunol. Meth.* 257: 175-184).

(2) Cell Culture

MCF10A cells were cultured in Dulbecco's modified Eagle's medium (DMEM)/F12 supplemented with 2.5% FBS, 1% penicillin-streptomycin, 0.1 µg/ml cholera toxin, 0.5 µg/ml hydrocortisone, 20 ng/ml epidermal growth factor (EGF), and 10 µg/ml serum insulin. A431 cells were grown in DMEM supplemented with 10% FBS and 1% penicillin-streptomycin. FaDu cells were cultured in Eagle's minimum essential medium (EMEM) supplemented with 10% FBS and 1% streptomycin-penicillin.

(3) X-Ray Irradiation and Drugs

After the growth to confluence, the cells were irradiated at 10Gy (3 mA/50 kV) in cabinet-type X-ray apparatus (SOFRON, soft X-ray inversion system). At a desired timing after irradiation, the cells were harvested. Stock solutions of roscovitine (100 mM), caffeine (100 mM), wortmannin (1 mM), CPT (29 mM, DMSO), MMC (0.5 mg/ml, PBS), carboplatin (0.1 mg/ml), hydroxyurea (1M, PBS), and aphidicolin (10 µM) were added to the culture medium of the cells so as to achieve predetermined concentrations.

(4) Screening of the Antibody Library

Screening was performed according to ICOS (Akahori et al., 2009, *Biochem. Biophys. Res. Commun.* 378: 832-835) in a manner modified as follows. The X-ray-irradiated cells ($1 \times 10^8$ cells in total) were incubated in Solution A (1.6 ml; 1% BSA, MEM, and 0.1% NaN$_3$) with phages (0.5 to $1 \times 10^{13}$ cfu) from the AIMS5 library. The suspension of the cells and phages were placed on an organic solution and cell-phage complexes were recovered by centrifugation. The obtained complexes were resuspended in solution A. After this process was repeated three times, the complexes were mixed with *E. coli* DH12S for phage preparation. This screening was repeated again. Phages recovered from the screening of the second round were mixed with non-irradiated cells ($1\times10^8$ cells). The screening process was further repeated. At the end of the screening of the third round, polyclonal antibodies were prepared from the recovered phages in order to make them play the role of a masking agent. At this stage, scFv-$C_L$ fused with cp3 was converted to scFv-$C_L$ (scFv-$C_L$-PP) fused with the protein A domain (Ito and Kurosawa, 1993, *J. Biol. Chem.* 268: 20668-20675). Polyclonal antibodies in the form of scFv-$C_L$-PP were produced and purified as a masking agent. The X-ray irradiated cells ($1\times10^8$ cells in total) were incubated with the masking agent containing 500 µg of the antibodies at 4° C. for 4 hours, and then $3\times10^{10}$ phages were recovered by the screening of the first round. After incubation, ICOS was performed. This screening round was repeated again to support masking. At the end, *E. coli* DH12S cells infected with the recovered phages were seeded on a plate. About 300 colonies were selected. For further analysis, the monoclonal antibodies in the forms of cp3 and PP were prepared from the individual phages (5) Screening of Positive Phages by ELISA X-ray-irradiated cells and non-irradiated cells were prepared, and antibodies specific to the irradiated cells were screened for by cell ELISA. That is, reactivity of antibody to both cells was examined by ELISA. A blocking solution (5% skim milk/0.05% $NaN_3$/PBS) was added at 200 µL/well to both cells, followed by blocking at 37° C. for 2 hours. The blocking solution was removed and the cells were washed with PBS. The supernatant of the above antibody expression culture was added at 100 µL/well, followed by reaction at 37° C. for 1 hour. The resultant was washed five times with PBS. Rabbit anti-cp3 (1 µg/mL) diluted with PBS/0.05% Tween 20 was added at 100 µL/well, followed by reaction at 37° C. for 1 hour. The resultant was washed five times with PBS. Anti-Rabbit IgG (H+L)-HRP diluted 2000-fold with PBS/0.05% Tween 20 was further added at 100 µL/well, followed by reaction at 37° C. for 1 hour. The resultant was washed five times with PBS. OPD in 0.1 M citrate phosphate buffer (pH5.1)+0.01% $H_2O_2$ was added at 100 µL/well, followed by reaction at room temperature for 5 minutes. $2NH_2SO_2$ was added at 100 µL/well to stop color development. Then, the absorbance at 492 nm was measured by SPECTRAmax340PC (Molecular Devices). Antibodies showing obvious positive reactivity specific to only the irradiated cells were selected and DNA sequences of the phages were analyzed. As a result, new phage antibodies were obtained.

(6) Flow Cytometry (FCM)

The FCM analysis was carried out according to the method reported previously (Kurosawa et al., 2009, *Immunol. Meth.* 351: 1-12). Reactivity of the obtained anti-Ly6D antibodies was examined using the Ly6D expression cell line, namely A431™ (cell line human squamous carcinoma) (CML ATCC CCL-243). The A431 cells were recovered by centrifugation. The recovered cells were washed once with PBS and then suspended in FACS Buffer (PBS containing 1% BSA, 2 mM EDTA, and 0.1% NaN3) to result in $1\times10^6$ cells/mL. The cell suspension (100 µL) was dispensed on a 96-well V-bottomed plate (Costar 3897). The Ly6D antibodies were adjusted to a concentration of 0.02 to 2 µg/mL using FACS Buffer. The prepared antibody solution (100 µL) was added to the cells, followed by incubation at 4° C. for 1 hour. The cells were washed twice with FACS buffer. Then, 100 µL of ALEX-AFLUOR-anti-human IgG™ (fluorescent antibody) (Invitrogen) diluted 750-fold with FACS Buffer was added to the cells, followed by another incubation at 4° C. for 1 hour. The cells were washed with FACS Buffer twice by centrifugation and set in HTS of FACS Calibur (BD) for measurement of FL1 fluorescence intensity of each well.

(7) Immunofluorescence

The cells were grown on sterilized glass coverslips set in a 6-well plate to reach a confluence of 50% to 75%. Before immunostaining, the cells were washed with TBS and incubated at room temperature for 15 minutes with a 1% BSA/TBS blocking solution. Then, the cells were incubated with primary antibodies (5 to 10 µg/ml) at 37° C. for 1 hour. Next, the coverslips were washed twice with TBS. The cells were incubated with secondary antibodies (2 µg/ml) at 37° C. for 30 minutes. The cells were fixed for 10 minutes with a 4% formaldehyde solution. The coverslips were placed on glass slides using a mount agent containing DAPI.

(8) Immunoprecipitation (IP) and Mass Spectrometry

Conditions of immunoprecipitation were set as previously reported (Kurosawa et al., 2009, *J. Immunol. Meth.* 351: 1-12). According to the phase transfer surfactant (PTS) protocol for in-solution digestion (Masuda et al., 2009, *Mol. Cell. Proteomics* 8: 2770-2777; and Iwasaki et al., 2009, *J. Proteome Res.* 8: 3169-3175), the immunoprecipitation product was digested with trypsin (Promega, Madison, Wis.) and LYS-C™ (protease) (WAKO Pure Chemical, Osaka, Japan) and concentrated using C18 STAGETIPS™ (pipette tips) (Thermo-Fisher Scientific, Waltham, Mass.). The concentrate was analyzed by LC/MS.

(9) PI-PLC Treatment

Biotinylated cells ($1\times10^7$ cells) were washed with PBS and then treated with 1 U/ml of PI-PLC (Sigma) in 1 ml of PBS at 37° C. for 1 hour. The cells were centrifuged and the supernatant and cell pellets were separately subjected to immunoprecipitation.

(10) siRNA

Stealth (trademark) RNAi (5'-UCCAAGUCAUCAGCA-UUCCAUGCCC-3') (SEQ ID NO: 14) targeting Ly6D was designed using BLOCK-iT (trademark) RNAi designer (Invitrogen). The following were purchased from Thermo Scientific: siGENOME SMARTpool siRNA targeting DNA-PK siRNA (A1: GCAAAGAGGUGGCAGUUAA (SEQ ID NO: 15); A2: GAGCAUCACUUGCCUUUAA (SEQ ID NO: 16); A3: GAUGAGAAGUCCUUAGGUA (SEQ ID NO: 17); and A4: GCAGGACCGUGCAAGGUUA (SEQ ID NO: 18)), ATM siRNA (B1: GCAAAGCCCUAGUAACAUA (SEQ ID NO: 19); B2: GGGCAUUACGGGUGUUGAA (SEQ ID NO: 20); B3: UCGCUUAGCAGGAGGUGUA (SEQ ID NO: 21); and B4: UGAUGAAGAGAGACGGAAU (SEQ ID NO: 22)), and ATR siRNA (C1: GAACAACACUGCUGGU-UUG (SEQ ID NO: 23); C2: GCAACUCGCCUAACA-GAUA (SEQ ID NO: 24); C3: UCUCAGAAGUCAAC-CGAUU (SEQ ID NO: 25); and C4: GAAUUGUGUUGCAGAGCUU (SEQ ID NO: 26)); and ON-TARGET plus SMART Pool siRNA targeting CHEK1 (D1: CAAGAUGUGUGGUACUUUA (SEQ ID NO: 27);

D2: GAGAAGGCAAUAUCCAAUA (SEQ ID NO: 28); D3: CCACAUGUCCUGAUCAUAU (SEQ ID NO: 29); and D4: GAAGUUGGGCUAUCAAUGG (SEQ ID NO: 30)) and CHEK2 (E1: CUCAGGAACUCUAUUCUAU (SEQ ID NO: 31); E2: GUUGUGAACUCCGUGGUUU (SEQ ID NO: 32); E3: GCAUAGGACUCAAGUGUCA (SEQ ID NO: 33); and E4: GUAAGAAAGUAGCCAUAAA (34 SEQ ID NO)). p53 siRNA (5'-CAGUCUACCUCCCGCCAUA-3'(SEQ ID NO: 35)) was purchased from Eurofins MWG Operon. All-Stars RNAi control (QIAGEN) was used for a negative control. Either lipofectamin (trademark) RNAiMAX (Invitrogen) or DharmaFECT (ThermoScientific) was used according to the manufacturer's protocol to cause siRNA double strand (25 nM) to transiently transfect with the cells for two days.

(11) Real-Time PCR

MCF10A cells were X-ray irradiated at 10 Gy and then cultured for 24 hours. Total RNA extraction was performed using a QUICKGENERNA™ cultured cell kit S (FUJIFILM). cDNA was synthesized using SUPERSCRIPT™ III reverse transcriptase (lnvitrogen). Quantitative reverse transcription PCR (qRT-PCR) was performed using SYBR Green Master Mix™ (PCR dye) according to the manufacturer's instructions. As an internal control, glyceraldehyde-3-phosphate dehydrogenase (GAPDH) was used. Ly6D primers were designed as previously reported (Nieuwenhuis et al., 2003, Lab. Invest. 83: 1233-1240). The following are specific primers synthesized by SIGMA: the forward primer (5'-AGATGAGGACAGCATTGCTGC-3' (SEQ ID NO: 36)) and the reverse primer (5'-GCAGACCACAGAATGCTTGC-3' (SEQ ID NO: 37)) of Ly6D; and the forward primer (5'-ACTTCAACAGCGACACCCAC-3' (SEQ ID NO: 38)) and the reverse primer (5'-CAACTGTGAGGAGGGGAGAT-3' (SEQ ID NO: 39)) of GADPH.

(12) Logic of Masking Strategy

As described above, the antibody library (AIMS5 consisting of independent $1\times10^{11}$ clones) was screened twice with X-ray-irradiated MCF10A cells and once with non-irradiated MCF10A cells. A phage fraction isolated and obtained at the end of screening was pooled and converted into scFv-CL-PP. At this stage, the numbers of outputs of screening were $1.5\times10^6$, $3.4\times10^6$, and $9\times10^6$ and thus the fluctuation in the number of clones was estimated to be $1\times10^5$ or less. Assuming that the total number of epitopes on the membrane protein would be 2000 to 3000, epitopes recognized by 200 to 300 clones could be dominant and present on X-ray-irradiated MCF10A cells and non-irradiated MCF10A cells so as to be masked on a priority basis. In this Example, 1.6 ml of a solution containing 500 μg of total protein was used as a masking agent. Since the molecular weight of scFv-$C_L$-PP is 50 kDa, the masking agent corresponds to $6\times10^{15}$ molecules. Based on many experiences of screening of cancer cells, a half of antibodies in the masking agent were estimated to bind to dominant epitopes. This estimate indicates that $1.5\times10^{13}$ antibody molecules for a dominant epitope exist in 1.6 ml of a solution for the dominant epitope, resulting in a masking antibody concentration of 15 nM. In addition, $1\times10^8$ cells were used for screening. Assuming that the number of dominant epitopes on a cell surface is $10^4$, each concentration of epitopes is estimated to be 1 nM. Accordingly, the concentration of the masking antibody could be much higher than the concentration of a target antigen. Since the antigen/antibody equilibrium is determined by the antibody concentration, antigens were covered with the masking antibodies at a rate of 90% on average in the experiment of this Example.

(13) Supplementary Information

Table 1 lists proteins identified by MS. The entire complementary sequences of the proteins obtained by immunoprecipitation of X-ray-irradiated and non-irradiated MCF10A cells were digested with trypsin, followed by MS analysis. As antibodies for immunoprecipitation, E33-139 and E33-026 clones were used separately. Only proteins that could exist with more than 98% probability are listed in this table. For proteins identified in the past, experiments in which a variety of cell compartments were analyzed are marked at the respective columns for cell compartments.

TABLE 1

| # | Visible? | Starred? | Bio View: Identified Proteins (150) | Acession Number | Molecular Weight | Protein Grouping Ambiguity | Taxonomy | Golgi apparatus | cytoplasm | cytoskeleton | endoplasmic reticulum | endosome | extracellular region | intracellular organelle | membrane | mitochondrion |
|---|---|---|---|---|---|---|---|---|---|---|---|---|---|---|---|---|
| 1 | ☑ | | 40S ribosomal protein S3 ... | RS3_HUMAN | 27 kDa | | Homo... | | ⁕ | | | | | ⁕ | ⁕ | |
| 2 | ☑ | | 60 kDa heat shook prote ... | GH60_HUM... | 61 kDa | | Homo... | ⁕ | | | ⁕ | | ⁕ | ⁕ | ⁕ | ⁕ |
| 3 | ☑ | | Myosin-9 OS=Homo sapi ... | MYH9_HU... | 227 kDa | ★ | Homo... | | ⁕ | ⁕ | | | | ⁕ | ⁕ | |
| 4 | ☑ | | Alpha-enolase OS=Homo ... | ENOA_HU... | 47 kDa | | Homo... | | ⁕ | | | | | ⁕ | ⁕ | |
| 5 | ☑ | | Annexin A2 OS=Homo sa ... | ANXA2_HU... | 39 kDa | | Homo... | | ⁕ | | | ⁕ | ⁕ | ⁕ | ⁕ | |
| 6 | ☑ | | Guanine nucleotide-bindi ... | GBLP_HUM... | 35 kDa | | Homo... | | ⁕ | | | | | ⁕ | | |
| 7 | ☑ | | Keratin, type II cytoskele ... | K2C1_HUM... | 66 kDa | ★ | Homo... | | | ⁕ | | | | ⁕ | ⁕ | |
| 8 | ☑ | | ATP synthase subunit al ... | ATPA_HU... | 60 kDa | | Homo... | | ⁕ | | | | | ⁕ | ⁕ | ⁕ |
| 9 | ☑ | | Filamin-A OS=Homo sap ... | FLNA_HUM... | 281 kDa | ★ | Homo... | ⁕ | ⁕ | ⁕ | | | ⁕ | ⁕ | | |
| 10 | ☑ | | ATP synthase subunit be ... | ATPB_HU... | 57 kDa | | Homo... | | ⁕ | | | | | ⁕ | ⁕ | ⁕ |
| 11 | ☑ | | ATP-dependent RNA hell ... | DDX3X_HU... | 73 kDa | | Homo... | | ⁕ | | | | | ⁕ | | |
| 12 | ☑ | | ADP-ribosylation factor ... | ARF4_HUM... | 21 kDa | ★ | Homo... | ⁕ | ⁕ | | | | | ⁕ | ⁕ | |
| 13 | ☑ | | ATP synthase subunit O ... | ATPO_HU... | 23 kDa | | Homo... | | ⁕ | | | | | ⁕ | ⁕ | ⁕ |
| 14 | ☑ | | 40S ribosomal protein S ... | RSSA_HU... | 33 kDa | | Homo... | | ⁕ | | | | | ⁕ | ⁕ | |
| 15 | ☑ | | ADP-ribosylation factor ... | ARF1_HUM... | 21 kDa | ★ | Homo... | ⁕ | ⁕ | | | | | ⁕ | ⁕ | |
| 16 | ☑ | | Pleotin OS=Homo sapi ... | PLEC1_HU... | 532 kDa | ★ | Homo... | | ⁕ | ⁕ | | | | ⁕ | ⁕ | |
| 17 | ☑ | | T-complex protein 1 sub ... | TOPG_HU... | 61 kDa | | Homo... | | ⁕ | | | | | ⁕ | ⁕ | |
| 18 | ☑ | | Heat shock protein beta ... | HSPB1_HU... | 23 kDa | | Homo... | | ⁕ | ⁕ | | | | ⁕ | ⁕ | |
| 19 | ☑ | | Lamin-A/O OS=Homo sa ... | LMNA_HU... | 74 kDa | | Homo... | | ⁕ | ⁕ | | | | ⁕ | | |
| 20 | ☑ | | ADP-ribosylation factor ... | ARF6_HUM... | 20 kDa | | Homo... | ⁕ | ⁕ | | | ⁕ | | ⁕ | ⁕ | |

TABLE 1-continued

| # | ✓ | Name | ID | Size | * | Species |
|---|---|---|---|---|---|---|
| 21 | ✓ | Calmodulin OS=Homo sa... | CALM_HU... | 17 kDa | | Homo... |
| 22 | ✓ | Complement Component... | C1QBP_HU... | 31 kDa | | Homo... |
| 23 | ✓ | Lymphocyte antigen 6D... | LY6D_HUM... | 13 kDa | | Homo... |
| 24 | ✓ | ADP/ATP transloicase 2... | ADT2_HUM... | 33 kDa | ★ | Homo... |
| 25 | ✓ | LanC-like protein 1 OS=... | LANC1_HU... | 45 kDa | | Homo... |
| 26 | ✓ | Four and a half LIM dom... | FHL2_HUM... | 32 kDa | | Homo... |
| 27 | ✓ | Desmoplakin OS=Homo s... | DESP_HUM... | 332 kDa | | Homo... |
| 28 | ✓ | Actin, cytoplasmic 1 OS... | ACTB_HUM... | 42 kDa | ★ | Homo... |
| 29 | ✓ | Pyruvate kinase isozyme... | KPYM_HU... | 58 kDa | | Homo... |
| 30 | ✓ | Tubulin beta-2O chain O... | TBB2O_HU... | 50 kDa | ★ | Homo... |
| 31 | ✓ | Stress-70 protein, mitoc... | GRP75_HU... | 74 kDa | | Homo... |
| 32 | ✓ | Tubulin alpha-1B chain... | TBA1B_HU... | 50 kDa | ★ | Homo... |
| 33 | ✓ | Heat shock cognate 71 k... | HSP7O_HU... | 71 kDa | ★ | Homo... |
| 34 | ✓ | Elongation factor 1-alph... | EF1A1_HU... | 50 kDa | | Homo... |
| 35 | ✓ | Peroxiredoxin-1 OS=Hom... | PRDX1_HU... | 22 kDa | ★ | Homo... |
| 36 | ✓ | Protein-L-isoaspartate(... | PIMT_HUM... | 25 kDa | | Homo... |
| 37 | ✓ | Ig kappa chain C region... | IGKC_HUM... | 12 kDa | | Homo... |
| 38 | ✓ | Glyceraldehyde-3-phosp... | G3P_HUMAN | 36 kDa | | Homo... |
| 39 | ✓ | 40S ribosomal protein S1... | RS18_HUM... | 18 kDa | | Homo... |
| 40 | ✓ | Heterogeneous nuclear ri... | HNRH1_HU... | 49 kDa | ★ | Homo... |
| 41 | ✓ | Cofilin-1 OS=Homo sapi... | COF1_HU... | 19 kDa | | Homo... |
| 42 | ✓ | Poly(U)-binding-splicing... | PUF60_HUM... | 60 kDa | | Homo... |
| 43 | ✓ | Galectin-1 OS=Homo sa... | LEG1_HUM... | 15 kDa | | Homo... |
| 44 | ✓ | Tubulin beta chain OS=H... | TBB5_HUM... | 50 kDa | ★ | Homo... |
| 45 | ✓ | Fatty solid synthase OS=... | FAS_HUM... | 273 kDa | | Homo... |
| 46 | ✓ | Keratin, type I cytoskelet... | K1C9_HUM... | 62 kDa | ★ | Homo... |
| 47 | ✓ | Elongation factor 2 OS=... | EF2_HUMAN | 95 kDa | | Homo... |
| 48 | ✓ | Ig gamma-1 chain O regi... | IGHG1_HU... | 36 kDa | ★ | Homo... |
| 49 | ✓ | Myosin regulatory light c | ML12A_HU... | 20 kDa | | Homo... |
| 50 | ✓ | ATP-dependent RNA heli... | DDX1_HUM... | 82 kDa | | Homo... |
| 51 | ✓ | 40S ribosomal protein S5... | RS5_HUMAN | 23 kDa | | Homo... |
| 52 | ✓ | Myosin light polypeptide... | MYL6_HUM... | 17 kDa | | Homo... |
| 53 | ✓ | Heat shock protein HSP... | HS90B_HU... | 83 kDa | | Homo... |
| 54 | ✓ | GTP-binding nuclear pro... | RAN_HUM... | 24 kDa | | Homo... |
| 55 | ✓ | Ig lambda chain C region... | LAC_HUM... | 11 kDa | | Homo... |
| 56 | ✓ | Poly(rO)-binding protein... | POBP1_HU... | 37 kDa | ★ | Homo... |
| 57 | ✓ | Elongation factor Tu, mit... | EFTU_HUM... | 50 kDa | | Homo... |
| 58 | ✓ | Thioredoxin OS=Homo sa... | THIO_HUM... | 12 kDa | | Homo... |
| 59 | ✓ | RuvB-like 2 OS=Homo s... | RUVB2_HU... | 15 kDa | | Homo... |
| 60 | ✓ | Cytochrome b-o1 comple... | QCR2_HU... | 48 kDa | | Homo... |
| 61 | ✓ | 60S ribosomal protein L1... | RL11_HUM... | 20 kDa | | Homo... |
| 62 | ✓ | Keratin, type I cytoskelet... | K1C10_HU... | 59 kDa | ★ | Homo... |
| 63 | ✓ | 40S ribosomal protein S1... | RS17_HUM... | 16 kDa | | Homo... |
| 64 | ✓ | Nicotinamide phosphorib... | NAMPT_H... | 56 kDa | | Homo... |
| 65 | ✓ | 40S ribosomal protein S1... | RS19_HUM... | 16 kDa | | Homo... |
| 66 | ✓ | UPF0568 protein C14orf1... | CN165_HU... | 28 kDa | | Homo... |
| 67 | ✓ | Peptidyl-prolyl cis-trans... | PPIA_HUM... | 18 kDa | | Homo... |
| 68 | ✓ | Destrin OS=Homo sapien... | DEST_HUM... | 19 kDa | | Homo... |
| 69 | ✓ | 40S ribosomal protein S2... | RS20_HUM... | 13 kDa | | Homo... |
| 70 | ✓ | Peroxiredoxin-2 OS=Hom... | PRDX2_HU... | 22 kDa | ★ | Homo... |
| 71 | ✓ | Keratin, type II cuticular... | KRT81_HU... | 55 kDa | | Homo... |
| 72 | ✓ | RNA-binding protein FU... | FUS_HUM... | 53 kDa | | Homo... |
| 73 | ✓ | UPF0027 protein C22orf2... | CV028_HU... | 55 kDa | | Homo... |
| 74 | ✓ | Keratin, type I cytoskelet... | K1C14_HU... | 52 kDa | ★ | Homo... |
| 75 | ✓ | 78 kDa glucose-regulate... | GRP78_HU... | 72 kDa | ★ | Homo... |
| 76 | ✓ | Tubulin alpha-1C chain... | TBA1C_HU... | 50 kDa | ★ | Homo... |
| 77 | ✓ | Poly(rC)-binding protein... | PCBP2_HU... | 39 kDa | ★ | Homo... |
| 78 | ✓ | T-complex protein 1 sub... | TCPA_HU... | 60 kDa | | Homo... |
| 79 | ✓ | Eukaryotic initiation fact... | IF4A1_HU... | 46 kDa | | Homo... |
| 80 | ✓ | Eukaryotic translation in... | IF5A1_HU... | 17 kDa | | Homo... |
| 81 | ✓ | 40S ribosomal protein S1... | RS12_HUM... | 15 kDa | | Homo... |
| 82 | ✓ | Myosin-10 OS=Homo sap... | MYH10_HU... | 229 kDa | ★ | Homo... |
| 83 | ✓ | Heat shock 70 kDa prote... | HSP71_HU... | 70 kDa | ★ | Homo... |
| 84 | ✓ | Glycyl-tRNA synthetase... | SYG_HUM... | 83 kDa | | Homo... |
| 85 | ✓ | RuvB-like 1 OS=Homo s... | RUVB1_HU... | 50 kDa | | Homo... |
| 86 | ✓ | 60S ribosomal protein L1... | RL12_HUM... | 18 kDa | | Homo... |
| 87 | ✓ | Peroxiredoxin-6 OS=Hom... | PRDX6_HU... | 25 kDa | | Homo... |
| 88 | ✓ | Coiled-coil-helix-coiled... | CHCH1_HU... | 13 kDa | | Homo... |

TABLE 1-continued

| # | ✓ | Name | ID | Size | ★ | Species | c1 | c2 | c3 | c4 | c5 |
|---|---|---|---|---|---|---|---|---|---|---|---|
| 89 | ☑ | Ig gamma-2 chain C regi... | IGHG2_HU... | 36 kDa | ★ | Homo... | | | | | |
| 90 | ☑ | Inosine-5′-monophosphat... | IMDH2_HU... | 56 kDa | | Homo... | | | | ※ | |
| 91 | ☑ | Multifunctional protein A... | PUR6_HUM... | 47 kDa | | Homo... | | | | | |
| 92 | ☑ | 40S ribosomal protein S1... | RS15A_HU... | 15 kDa | | Homo... | ※ | | | ※ | |
| 93 | ☑ | Tropomyosin alpha-3 cha... | TPM3_HUM... | 33 kDa | ★ | Homo... | ※ | ※ | | ※ | |
| 94 | ☑ | Keratin, type II cytoskele... | K2C5_HUM... | 62 kDa | ★ | Homo... | | ※ | | ※ | |
| 95 | ☑ | C-1-tetrahydrofolate syn... | C1TC_HUM... | 102 kDa | | Homo... | ※ | | | ※ | ※ |
| 96 | ☑ | Cysteine and glycine-ric... | CSRP1_HU... | 21 kDa | | Homo... | | | | | |
| 97 | ☑ | Tubulin alpha-4A chain... | TBA4A_HU... | 50 kDa | | Homo... | ※ | ※ | ※ | ※ | |
| 98 | ☑ | Activated RNA polymers... | TCP4_HUM... | 14 kDa | | Homo... | | | | ※ | |
| 99 | ☑ | Cytochrom b-c1 comple... | QCR1_HU... | 53 kDa | | Homo... | ※ | | | ※ | ※ |
| 100 | ☑ | Ribonuclease inhibitor O... | RINI_HUM... | 50 kDa | ★ | Homo... | ※ | | ※ | | |
| 101 | ☑ | 6-phosphofructokinase t... | K6PP_HUM... | 86 kDa | | Homo... | ※ | | | | |
| 102 | ☑ | Sideroflexin-1 OS=Homo... | SFXN1_HU... | 36 kDa | | Homo... | ※ | | | ※ | ※ |
| 103 | ☑ | Creatine kinase U-type,... | KCRU_HU... | 47 kDa | | Homo... | ※ | | | ※ | ※ |
| 104 | ☑ | Heterogeneous nuclear ri... | HNRPK_HU... | 51 kDa | | Homo... | ※ | | | ※ | |
| 105 | ☑ | High mobility group prot... | HMGB1_H... | 25 kDa | | Homo... | ※ | | | | |
| 106 | ☑ | ATP synthase subunit ge... | ATPG_HU... | 33 kDa | | Homo... | ※ | | | ※ | ※ |
| 107 | ☑ | Glutathione S-transferase... | GSTP1_HU... | 23 kDa | | Homo... | ※ | | | | |
| 108 | ☑ | Protein TFG OS=Homo s... | TFG_HUM... | 43 kDa | | Homo... | ※ | | | | |
| 109 | ☑ | Proliferating cell nuclear... | PCNA_HU... | 29 kDa | | Homo... | | | | ※ | ※ |
| 110 | ☑ | 40S ribosomal protein S2... | RS29_HUM... | 7 kDa | | Homo... | ※ | | | ※ | |
| 111 | ☑ | ATP synthase subunit f,... | ATPK_HUM... | 11 kDa | | Homo... | | | | ※ | ※ |
| 112 | ☑ | Thioredoxin-dependent p... | PRDX3_HU... | 28 kDa | | Homo... | ※ | | ※ | ※ | ※ |
| 113 | ☑ | 40S ribosomal protein S2... | RS28_HUM... | 8 kDa | | Homo... | ※ | | | ※ | |
| 114 | ☑ | Nuceloside diphosphate... | NDKA_HU... | 17 kDa | | Homo... | ※ | ※ | | | |
| 115 | ☑ | Probable ATP-dependent... | DDX5_HUM... | 69 kDa | | Homo... | ※ | | | | |
| 116 | ☑ | Bifunctional methylenete... | MTDC_HU... | 38 kDa | | Homo... | ※ | | | ※ | ※ |
| 117 | ☑ | Leucine-rich repeat-cont... | LRC59_HU... | 35 kDa | | Homo... | ※ | | ※ | ※ | ※ |
| 118 | ☑ | 40S ribosomal protein S1... | RS10_HUM... | 19 kDa | ★ | Homo... | ※ | | | ※ | |
| 119 | ☑ | Nucleoside-triphosphate... | CA057_HU... | 21 kDa | | Homo... | | | | | |
| 120 | ☑ | NADH dehydrogenase [u... | NDUB4_HU... | 15 kDa | | Homo... | ※ | | | ※ | ※ |
| 121 | ☑ | Adenosylhomocysteinase... | SAHH_HU... | 48 kDa | | Homo... | ※ | | ※ | | |
| 122 | ☑ | D-3-phosphoglycerate d... | SERA_HU... | 57 kDa | | Homo... | | | | | |
| 123 | ☑ | Succinate dyhydrogenase... | DHSA_HU... | 73 kDa | | Homo... | ※ | | | ※ | |
| 124 | ☑ | 60S acidic ribosomal pro... | RLA2_HUM... | 12 kDa | | Homo... | ※ | | | ※ | |
| 125 | ☑ | Bifunctional aminoacyl-t... | SYEP_HUM... | 171 kDa | | Homo... | ※ | | | | |
| 126 | ☑ | Filamin-B OS=Homo sap... | FLNB_HUM... | 278 kDa | ★ | Homo... | ※ | ※ | | ※ | ※ |
| 127 | ☑ | Isoleucyl-tRNA syntheta... | SYM_HUM... | 114 kDa | | Homo... | ※ | | | ※ | ※ |
| 128 | ☑ | Glycogen phosphorylase,... | PYGB_HUM... | 97 kDa | | Homo... | ※ | | | | |
| 129 | ☑ | Protein FAM98B OS=Ho... | FA98B_HU... | 37 kDa | | Homo... | | | | | |
| 130 | ☑ | Protein scribble homolog... | SCRIB_HU... | 175 kDa | | unkno... | | | | | |
| 131 | ☑ | F-actin-capping protein... | GAZA1_HU... | 33 kDa | | Homo... | ※ | | | ※ | |
| 132 | ☑ | T-complex protein 1 sub... | TCPE_HUM... | 60 kDa | | Homo... | ※ | | | ※ | |
| 133 | ☑ | 60S ribosomal protein L3... | RL38_HUM... | 8 kDa | | Homo... | ※ | | | ※ | |
| 134 | ☑ | Trifunctional purine bios... | PUR2_HUM... | 108 kDa | | Homo... | ※ | | | | |
| 135 | ☑ | Tropomycein alpha-4 cha... | TPM4_HUM... | 29 kDa | ★ | Homo... | ※ | ※ | | ※ | ※ |
| 136 | ☑ | 40S ribosomal protein S1... | RS16_HUM... | 16 kDa | | Homo... | ※ | | | | |
| 137 | ☑ | Nesprin-1 OS=Homo sap... | SYNE1_HU... | 1011 kDa | | Homo... | ※ | ※ | | ※ | ※ |
| 138 | ☑ | Dolichyldiphosphatase 1... | DOPP1_HU... | 27 kDa | | Homo... | ※ | | ※ | ※ | ※ |
| 139 | ☑ | 60S acidic ribosomal pro... | RLA0_HUM... | 34 kDa | | Homo... | ※ | | | ※ | |
| 140 | ☑ | Inorganic pyrophosphate... | IPYR2_HU... | 38 kDa | | Homo... | ※ | | | ○ | ○ |
| 141 | ☑ | ATP synthase subunit g,... | ATP5I_HU... | 11 kDa | | Homo... | ※ | | | ※ | ※ |
| 142 | ☑ | Argininosuccinate syntha... | ASSY_HUM... | 47 kDa | | Homo... | ※ | | | | |
| 143 | ☑ | Mitogen-activated protei... | MK01_HUM... | 41 kDa | | Homo... | ※ | ※ | | ※ | |
| 144 | ☑ | Ryanodine receptor 3 OS... | RYR3_HUM... | 552 kDa | | Homo... | | | | ※ | |
| 145 | ☑ | Keratin, type II cytoskele... | K2C6A_HU... | 60 kDa | ★ | Homo... | | ※ | | | |
| 146 | ☑ | Keratin, type I cytoskelet... | K1C17_HU... | 48 kDa | ★ | Homo... | ※ | ※ | | ※ | |
| 147 | ☑ | ATP-binding cassette su... | ABCE1_HU... | 67 kDa | | Homo... | ※ | | | | ※ |
| 148 | ☑ | Myosin-Ib OS=Homo sapi... | MYO1B_H... | 132 kDa | | Homo... | ※ | | ※ | | |
| 149 | ☑ | UPF0585 protein C16orf1... | CP013_HU... | 25 kDa | | unkno... | | | | | |
| 150 | ☑ | TAR DNA-binding protei... | TADBP_HU... | 45 kDa | | Homo... | | | | ※ | |

TABLE 1-continued

| | Cellular Compartment | | | | | | | | |
|---|---|---|---|---|---|---|---|---|---|
| # | nucleus | organelle membrane | organelle part | plasma membrane | ribosome | 139x-ray | 139intact | 026x-ray | 026intact |
| 1 | ✸ | | | ✸ | ✸ | 100% | 100% | 100% | 100% |
| 2 | ✸ | ✸ | | ✸ | | 100% | 100% | 100% | 100% |
| 3 | ✸ | | ✸ | ✸ | | 100% | | 100% | 6% |
| 4 | ✸ | | | ✸ | | 100% | 100% | 100% | 100% |
| 5 | | | | ✸ | | 100% | 100% | 100% | 100% |
| 6 | | | | ✸ | | 100% | 100% | 100% | 100% |
| 7 | | | ✸ | ✸ | | 100% | 100% | 100% | 100% |
| 8 | | ✸ | | ✸ | | 100% | 100% | 100% | 100% |
| 9 | ✸ | | | ✸ | | 100% | 100% | 98% | 100% |
| 10 | | ✸ | | ✸ | | 100% | 100% | 100% | 100% |
| 11 | ✸ | | ✸ | ✸ | | 100% | 100% | 100% | 100% |
| 12 | | | | ✸ | | 100% | 100% | 100% | 100% |
| 13 | | ✸ | | ✸ | | 100% | 100% | 94% | 100% |
| 14 | ✸ | | | ✸ | ✸ | 100% | 99% | 100% | 100% |
| 15 | | ✸ | | ✸ | | 100% | 100% | 100% | 100% |
| 16 | | | | ✸ | | 100% | 100% | 100% | |
| 17 | ✸ | | | ✸ | | 100% | 99% | 99% | 100% |
| 18 | ✸ | | ✸ | ✸ | | 99% | 100% | 36% | 99% |
| 19 | ✸ | ✸ | | ✸ | | 100% | 100% | 50% | 92% |
| 20 | | | | ✸ | | 50% | 32% | 50% | 100% |
| 21 | ✸ | | | ✸ | | 100% | 98% | | |
| 22 | | | ✸ | ✸ | | | 11% | 100% | |
| 23 | | | | ✸ | | 100% | | | |
| 24 | | ✸ | ✸ | ✸ | | 100% | 100% | 100% | 100% |
| 25 | | | | ✸ | | 98% | 100% | 98% | 100% |
| 26 | ✸ | | | ✸ | | 100% | 100% | 100% | 100% |
| 27 | | | | ✸ | | 100% | 100% | | 100% |
| 28 | ✸ | | ✸ | | | 100% | 100% | 100% | 100% |
| 29 | ✸ | | | | | 100% | 100% | 100% | 100% |
| 30 | | | ✸ | | | 100% | 100% | 100% | 100% |
| 31 | | | ✸ | | | 100% | 100% | 100% | 100% |
| 32 | | | ✸ | | | 100% | 100% | 100% | 100% |
| 33 | | | | | | 100% | 100% | 100% | 100% |
| 34 | | | | | | 100% | 100% | 100% | 100% |
| 35 | ✸ | | | | | 100% | 100% | 100% | 100% |
| 36 | | | | | | 100% | 100% | 100% | 100% |
| 37 | | | | | | 100% | 100% | 100% | 100% |
| 38 | | | | | | 100% | 100% | 100% | 100% |
| 39 | | | ✸ | | ✸ | 100% | 100% | 100% | 100% |
| 40 | ✸ | | ✸ | | | 100% | 100% | 100% | 100% |
| 41 | ✸ | | ✸ | | | 100% | 100% | 100% | 100% |
| 42 | ✸ | | ✸ | | | 100% | 100% | 100% | 100% |
| 43 | | | | | | 100% | 100% | 100% | 100% |
| 44 | | | ✸ | | | 100% | 100% | 100% | 100% |
| 45 | | | | | | 100% | 100% | 100% | 100% |
| 46 | | | ✸ | | | 100% | 100% | 100% | 100% |
| 47 | | | | | | 100% | 100% | 100% | 100% |
| 48 | | | | | | 100% | 100% | 100% | 100% |
| 49 | | | ✸ | | | 100% | | 100% | |
| 50 | | | | | | 100% | 100% | 100% | 100% |
| 51 | | | ✸ | | ✸ | 100% | 100% | 100% | 100% |
| 52 | | | ✸ | | | 100% | 96% | 100% | 51% |
| 53 | | | ✸ | | | 100% | 100% | 100% | 100% |
| 54 | ✸ | | ✸ | | | 100% | 100% | 100% | 100% |
| 55 | | | | | | 100% | 100% | 50% | 100% |
| 56 | ✸ | | | | | 100% | 100% | 100% | 100% |
| 57 | | | ✸ | | | 100% | 100% | 100% | 100% |
| 58 | | | | | | 100% | 100% | 100% | 100% |
| 59 | ✸ | | ✸ | | | 100% | 100% | 100% | 100% |
| 60 | ✸ | ✸ | ✸ | | | 100% | 100% | 100% | 100% |
| 61 | ✸ | | ✸ | | ✸ | 100% | 100% | 100% | 100% |
| 62 | | | ✸ | | | 100% | 100% | 100% | 100% |
| 63 | | | ✸ | | ✸ | 100% | 100% | 16% | 100% |
| 64 | | | | | | 100% | 100% | 100% | 100% |
| 65 | ✸ | | ✸ | | ✸ | 100% | 100% | 100% | 100% |
| 66 | ✸ | | ✸ | | | 100% | 100% | 100% | 100% |
| 67 | ✸ | | | | | 100% | 100% | 100% | 100% |
| 68 | | | ✸ | | | 100% | 100% | 100% | 100% |
| 69 | | | ✸ | | ✸ | 100% | 100% | 100% | 100% |
| 70 | | | | | | 100% | 100% | 100% | 100% |
| 71 | | | ✸ | | | 100% | 100% | 100% | 100% |
| 72 | ✸ | | ✸ | | | 100% | 100% | 100% | 100% |
| 73 | | | | | | 100% | 100% | 100% | 100% |
| 74 | ✸ | | | | | 100% | 98% | 100% | 100% |
| 75 | ✸ | ✸ | | | | 100% | 100% | 100% | 100% |

TABLE 1-continued

| # | C1 | C2 | C3 | V1 | V2 | V3 | V4 |
|---|---|---|---|---|---|---|---|
| 76 | | | | 100% | 100% | 100% | 100% |
| 77 | ○ | ○ | | 100% | 100% | 100% | 100% |
| 78 | ○ | ○ | | 100% | 100% | 100% | 100% |
| 79 | | | | 100% | 100% | 100% | 100% |
| 80 | ○ | ○ | | 100% | 100% | 99% | 100% |
| 81 | | ○ | ○ | 100% | 100% | 100% | 100% |
| 82 | | ○ | | | | 100% | |
| 83 | ○ | | | 100% | 100% | 100% | 100% |
| 84 | | ○ | | 100% | 100% | 100% | 100% |
| 85 | ○ | ○ | | 99% | 100% | 98% | 100% |
| 86 | | | ○ | 100% | 100% | 99% | 100% |
| 87 | ○ | | | 100% | 100% | 100% | 99% |
| 88 | O | | | 100% | 100% | | |
| 89 | | | | 100% | 100% | 99% | 99% |
| 90 | | | | 100% | 99% | 98% | 99% |
| 91 | | | | 95% | 100% | 9% | 99% |
| 92 | | ○ | ○ | 100% | 100% | 100% | 100% |
| 93 | | ○ | | 100% | | 100% | |
| 94 | | ○ | | 100% | 98% | 99% | 99% |
| 95 | | | | 100% | 100% | | 100% |
| 96 | ○ | | | 100% | 99% | 99% | 99% |
| 97 | | ○ | | 100% | 100% | 100% | 51% |
| 98 | ○ | ○ | | 100% | 100% | 40% | 100% |
| 99 | | ○ | ○ | 50% | 47% | 93% | 100% |
| 100 | | | | 100% | 100% | 100% | 100% |
| 101 | | | | 100% | 50% | 94% | 99% |
| 102 | | ○ | ○ | 100% | 50% | 50% | 100% |
| 103 | | ○ | ○ | 100% | 50% | 50% | 100% |
| 104 | ○ | ○ | | 100% | 100% | | 99% |
| 105 | ○ | | ○ | 99% | 100% | | 99% |
| 106 | | ○ | ○ | 44% | 100% | 100% | 99% |
| 107 | | | | 46% | 100% | 19% | 51% |
| 108 | | | | 9% | 99% | 99% | 99% |
| 109 | ○ | ○ | ○ | 100% | | 100% | 100% |
| 110 | | | ○ | 100% | 100% | | 40% |
| 111 | ○ | ○ | | 50% | 98% | 7% | 51% |
| 112 | | | | 24% | 100% | 100% | 99% |
| 113 | | ○ | ○ | 99% | 99% | 50% | 51% |
| 114 | ○ | ○ | | 99% | 100% | 50% | 51% |
| 115 | ○ | ○ | | 100% | 50% | 50% | 51% |
| 116 | | | | 100% | 100% | | 100% |
| 117 | | ○ | | 99% | 99% | | 95% |
| 118 | | ○ | ○ | 100% | 99% | 41% | 51% |
| 119 | | | | 14% | | 94% | 99% |
| 120 | ○ | ○ | | | 5% | 98% | 99% |
| 121 | | | | 16% | | 93% | 99% |
| 122 | | | | | 98% | 9% | 98% |
| 123 | ○ | ○ | | 7% | 100% | 9% | 51% |
| 124 | | ○ | ○ | 100% | 100% | 50% | 51% |
| 125 | | | | 97% | 50% | 8% | 98% |
| 126 | | | | 97% | 93% | 18% | 7% |
| 127 | | ○ | | 97% | 7% | | 100% |
| 128 | | | | 34% | 1% | 36% | 99% |
| 129 | | | | 100% | 48% | | |
| 130 | | | | 100% | 32% | | |
| 131 | | ○ | | 100% | | 100% | |

TABLE 1-continued

| | | | | | | | |
|---|---|---|---|---|---|---|---|
| 132 | ◊ | | | | 97% | 50% | 20% | 51% |
| 133 | | | | ◊ | 13% | 100% | | 51% |
| 134 | | | | | | 50% | | 100% |
| 135 | | | ◊ | | 100% | | 50% | |
| 136 | | | | ◊ | 14% | 7% | 99% | 7% |
| 137 | ◊ | | ◊ | | 99% | 8% | | 12% |
| 138 | | ◊ | ◊ | | 99% | 13% | | |
| 139 | | | ◊ | ◊ | 99% | | | 97% |
| 140 | | | | | | 16% | 9% | 100% |
| 141 | | ◊ | ◊ | | | 17% | | 100% |
| 142 | | | | | 99% | | | |
| 143 | ◊ | | ◊ | | | | 21% | 98% |
| 144 | | | | | 100% | | | |
| 145 | | | ◊ | | 100% | | | |
| 146 | ◊ | | ◊ | | 100% | 100% | 100% | |
| 147 | | | | | | | | 99% |
| 148 | | | ◊ | | 99% | | | |
| 149 | | | | | | | | 99% |
| 150 | ◊ | | ◊ | | | | | 98% |

Probability Legend
- over 95%
- 80% to 94%
- 50% to 79%
- 20% to 49%
- 0% to 19%

(Results)

(1) Isolation of the E33-139 Monoclonal Antibody that Binds to Molecules on the Surfaces of MCF10A Cells Induced by X-Ray Irradiation In this Example, it was aimed to isolate a monoclonal antibody against the protein that is present on the surfaces of X-ray-irradiated cells but not present on the surfaces of non-irradiated cells. It is estimated that types and amounts of most of membrane proteins do not change before and after X-ray irradiation and thus the presence of the target protein is small. If X-ray-irradiated cells are simply mixed with the phages of the antibody library, the number of complexes formed with the target protein and the phage antibody would be too little to select the complexes efficiently by screening. To overcome this problem, the following screening strategy was adopted in the present invention. First, screening of the phage antibody library was performed in X-ray irradiation cells. Then, the screening was performed in non-irradiated cells. Consequently, the antibody of the phage fraction produced was found to bind to the membrane protein present on the surfaces of both X-ray-irradiated cells and non-irradiated cells. The distribution of each antibody reflected the amount of the target antigen. After screening, all antibodies were recovered and prepared as a masking agent. X-ray-irradiated cells were subjected to screening of the antibody library in the presence of the masking antibody in a large excess amount. It was estimated with this approach that relatively abundant membrane proteins present in both the X-ray-irradiated cells and non-irradiated cells should be masked on a priority basis, a probability of isolating the antibody that binds to the membrane protein present only in the X-ray-irradiated cells would increase.

Selection of clones from the antibody library was carried out as follows. After three instances of screening by X-ray-irradiated cells (the first screening in the absence of the masking antibody, and the second and third screenings in the presence of the masking antibody), 330 clones were selected. Among these clones, 205 clones were found to express an intact single-chain Fv (scFv) fragment on the phage surface. Sequence analysis showed that they are composed of different 136 types. Clones were selected by three different ways. By cell ELISA using X-ray irradiated cells and non-irradiated cells, 20 candidate clones were selected. FIG. 1A shows the results for 6 clones. As shown in FIG. 1A, the clones were found to bind to X-ray-irradiated cells more strongly than to non-irradiated cells. The 20 candidates were analyzed by flow cytometry (FCM). The fluorescence intensity of the X-ray-irradiated cells was consistently stronger than that of the non-irradiated cells and thus 6 clones were selected from them (FIG. 1B). At the end, the results of confocal laser microscope analysis showed that the E33-139 clone consistently and strongly binds to molecules present at a higher concentration than that for other molecules on the surfaces of the X-ray-irradiated cells (FIG. 1C). As described above, E33-139 was confirmed as an antibody that has no reactivity to MCF10A cells before X-ray irradiation and shows increased reactivity to MCF10A cells after X-ray irradiation.

FIG. 10 shows the amino acid sequence and the nucleotide sequence of the E33-139 antibody shown in SEQ ID NOS: 1 and 2 in the sequence listing. In addition, the amino acid sequences of the CDRs of the E33-139 antibody are shown in SEQ ID NOS: 3 to 8 in the sequence listing as follows: heavy chain CDR1 (SEQ ID NO: 3), heavy chain CDR2 (SEQ ID NO: 4), heavy chain CDR3 (SEQ ID NO: 5), light chain CDR1 (SEQ ID NO: 6), light chain CDR2 (SEQ ID NO: 7), and light chain CDR3 (SEQ ID NO: 8).

(2) LY6D is the Antigen Recognized by the E33-139 Antibody

Figure 2:
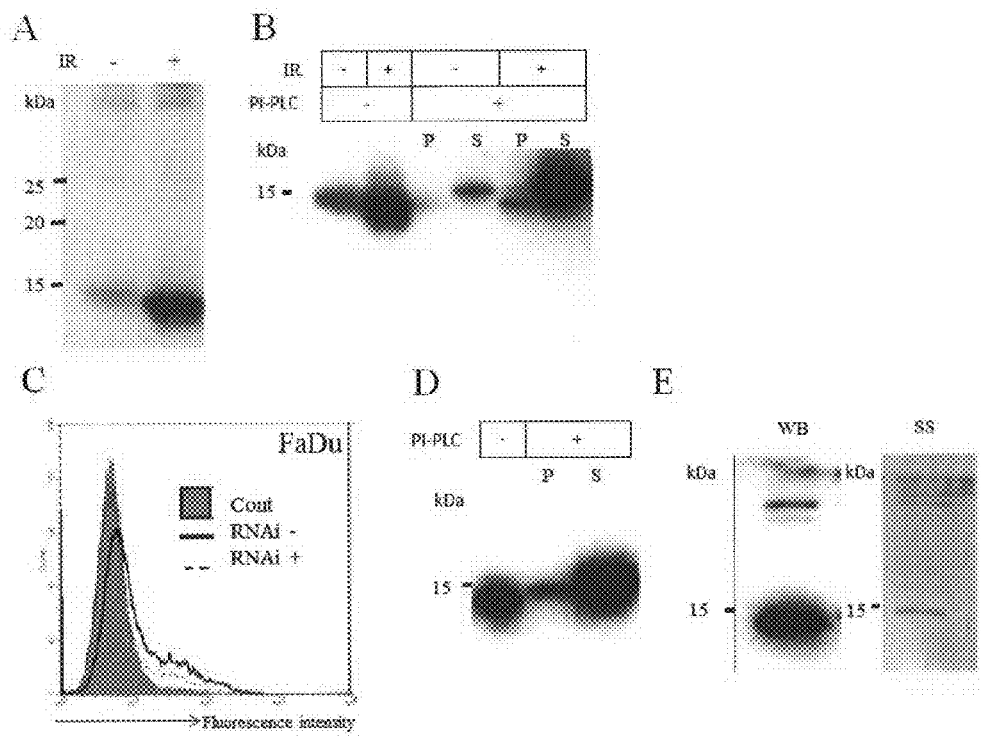
FIG. 2 shows the results of identification of a protein recognized by the E33-139 monoclonal antibody. After biotinylation, the membrane proteins of the X-ray-irradiated MCF10A cells (right) and non-irradiated MCF10A cells (left) were solubilized and subjected to immunoprecipitation using the E33-139 monoclonal antibody, the product was separated by SDS-PAGE, and western blot was performed with HRP-conjugated streptavidin (A: western blot). MCF10A cells treated as described above were digested with PI-PLC, the resultant was centrifuged, and cell pellets (P) and the supernatant (S) subjected to PI-PLC treatment were separately immunoprecipitated (B: western blot). FaDu cells were treated with LY6D siRNA or control siRNA and analyzed by FCM using the E33-139 monoclonal antibody (black line: control siRNA and the E33-139 monoclonal antibody; dashed line: LY6D siRNA and the E33-139 monoclonal antibody; gray: control siRNA without the E33-139 monoclonal antibody (C: FCM). The experiment shown in FIG. 2B was carried out using FaDu cells (D: western blot). Solubilized FaDu cells were subjected to IP using the E33-139 monoclonal antibody and the product was separated by SDS-PAGE (left: western blot using anti-hLY6D Ab (polyclonal Ab, commercial product); right: silver stained gel) (E: western blot).

Immunoprecipitation (IP) was performed to identify an antigen recognized by the E33-139 antibody. The molecules on the surfaces of X-ray-irradiated cells and non-irradiated cells were biotinylated and then solubilized with the addition of a surfactant. Immunoprecipitation was performed using the solubilized proteins and the resulting precipitate was subjected to SDS-PAGE. The gel was divided into two parts. One of them was silver stained and the other was subjected to western blot analysis so as to be examined by horseradish peroxidase (HRP)-conjugated streptavidin. As shown in FIG. 2A, the results of western blot analysis of samples prepared from X-ray-irradiated cells, a prominent band was observed at 14 kDa, while this band was slightly observed for samples prepared from non-irradiated cells. As a result of treatment of the immunoprecipitation product with trypsin or proteinase K before SDS-PAGE, the 14-kDa band disappeared, indicating that the product was a protein. As a result of silver staining, the quantity of the 14-kDa protein present in gel was found to be below the detection limit. Accordingly, the entire protein complements resulting from immunoprecipitation of both X-ray-irradiated cells and non-irradiated cells were digested with trypsin, followed by mass spectrometry (MS). As a result of MS analysis, 150 types of proteins were identified (Table 1). The majority of them were ribosomal proteins, myosin, actin, ATP synthase, heat shock proteins, and analogs thereof. They were identified based on the immunoprecipitation product derived from both X-ray-irradiated cells and non-irradiated cells. They were determined to be detected in precipitates in a nonspecific manner because they are abundant in the cytoplasm. Among the proteins identified by MS analysis, only LY6D was found to be a membrane protein. LY6D was identified by the precipitate derived from the X-ray-irradiated cells but it was not identified in the fraction derived from the non-irradiated cells. It was known that LY6D moves at 14 kDa in SDS-PAGE. Therefore, LY6D was determined to be a promising candidate as an antigen recognized by E33-139.

Since LY6D is a GPI-anchored protein (Brakenhoff et al., 1995, J. Cell Biol. 129: 1677-1689), X-ray-irradiated cells and non-irradiated cells were treated with phosphatidylinositol-specific phospholipase C (PI-PLC) after biotinylation of the membrane protein. PI-PLC-treated cells were harvested by centrifugation and the supernatant was preserved. Next, both proteins released into the supernatant and the cell lysate treated with a surfactant were subjected to immunoprecipitation. The precipitate was subjected to SDS-PAGE and western blot. As shown in. FIG. 2B, the majority of the 14-kDa band detected in the membrane fraction prior to treatment with PI-PLC was released into the supernatant. The results of SDS-PAGE after enzymatic digestion showed that the position of the band moved to 15 kDa. These results confirmed that the protein found at 14 kDa is a GPI-anchored protein.

In order to prove that antigen protein 139 detected by the E33-139 antibody is actually LY6D, at first, cells capable of abundantly expressing LY6D in the absence of X-ray irradiation were searched for. It has been reported that LY6D is abundantly expressed in a large amount in squamous cell carcinoma of head and neck (Quak et al., 1990, Am. J. Pathol. 136: 191-197). Flow cytometry results showed that FaDu cells express antigen protein 139 in a large amount; however, the degree of the expression was non-uniform in the cell population. The expression level of antigen protein 139 significantly decreased after injection of LY6D siRNA (FIG. 2C). The effects of PI-PLC treatment on FaDu cells were also investigated. Before digestion with PI-PLC, a 14-kDa band was detected by the western blot method. The band was released to the supernatant after enzymatic digestion, and the position of the band moved to 15 kD (FIG. 2D). The same immunoprecipitation sample was subjected to western blot. The resulting blots were detected using a commercially available anti-human LY6D antibody. A distinct 14 kDa band was detected by anti-human LY6D in the same position of the band detected in FIG. 2B. This protein band was visualized also by silver staining (FIG. 2E). These results concluded that antigen protein 139 is LY6D.

(3) Experiment for Confirming Binding with the Determined Antigen cDNA of Ly6D was prepared by PCR using a cancer cell line. cDNA of the Ly6D extracellular domain was prepared by a conventional method and inserted into PCMV-SCRIPT™ (vector) (Clontech Laboratories, Inc.). Thus, a soluble Ly6D antigen expression vector was prepared. This expression vector was introduced into the 293T cell line so as to prepare expression cells capable of producing a soluble Ly6D antigen.

Thereafter, ELISA was performed using the prepared Ly6D antigen.

Reactivity measurement of the Ly6D antibody by enzyme-linked immunosorbent assay (ELISA) was performed by adding the above forced-expressed recombinant as a solid phase antigen at 100 ng/well (a concentration of 1 µg/mL) to a plate and allowing the plate to stand overnight at 4° C. Next, BLOCKACE™ (blocking reagent composed of purified bovine milk proteins) was added at 200 µL/well, followed by blocking at room temperature for 1 hour. Then, a sample antibody was added to each well and incubated for 1 hour for reaction. The plate was washed 5 times with PBST (0.05% TWEEN20™ (polysorbate 20), PBS)). Goat anti-human IgG (H+L) (absorbed by mouse, rabbit, cow, or mouse IgG)-HRP (Cosmo Bio: AQI, Cat. A-11OPD) diluted 2000-fold with PBST was added as a detection antibody solution at 100 µL/well. After incubation for 1 hour, the plate was washed five times with PBST and then substrate buffer (TMB) was added at 100 µL/well. After incubation at room temperature in the dark for 15 minutes, a reaction stop solution was added at 100 µL/well to stop the reaction. Thereafter, the absorbance was measured at 450 nm.

(4) Conversion of the Phage Antibody (scFv) into IgG (4-1) Preparation of Plasmid Capable of Expressing the Anti-Ly6D IgG Antibody Conversion of the phage antibody into IgG was described below with reference to an example of conversion of the Ly6-DE33 clone into IgG. Conversion of other antibodies into IgG was performed in a similar manner.

The gene of the phage antibody (scFv) has an scFv structure in which VH and VL are arranged in such order and linked by a linker (SEQ ID NO: 9).

Table 2 shows the results of searching for the genes of the human germline estimated to be used in VH and VL of the Ly6D antibody by IMMUNOGENETICS™ (IMGT)(*).

TABLE 2

| VH | IGHV1-2*02 | IGHJ4*2 | IGHD4-17*01 |
| VL | IGLV1-51*01 | IGLJ3*02 | |

By referring to the search results of IMGT, conversion of the phage antibody into IgG was performed. VH of the anti-Ly6D antibody (SEQ ID NO: 10) was ligated to a constant region of human G1 (SEQ ID NO: 11). VL of the anti-Ly6D antibody (SEQ ID NO: 12) was ligated to IGLC3*01 (human light chain/ . . . constant region; SEQ ID NO: 13) arranged in parallel with the IGLJ3*2 gene. Thus, the gene sequence was prepared. Total synthesis of the H chain and L chain genes having Nhel at the 5' end and EcoRI at the 3' end was carried out by GenScript Inc. The synthesized heavy chain and light chain genes were separately incorporated into different expression vectors. Specifically, the artificially synthesized genes of the H chain and the L chain were cleaved with EcoRI and Nhel and incorporated into Nhel and EcoRI sites of the expression vector PCAGGS™ to obtain an anti-Ly6D030 antibody H-chain expression vector and an anti-Ly6D030 antibody L-chain expression vector.

(4-2) Transient Expression of the IgG Antibody

FREESTYLE™ (The media is serum-free, protein-free formulation designed to support the high-density culture and transfection of 293 cells in suspension. The media contains the dipeptide, L-alanyl-L-glutamine, a stabilized form of L-glutamine) was used for the transient expression of the IgG antibody. 293-F™ (The 293 cell line is a permanent line established from primary embryonal human kidney transformed with sheared human adenovirus type 5 DNA), which are floating cells for gene transfection, were subcultured on the day before transfection. On the day of transfection, 400 mL of a cell suspension adjusted to a cell concentration of $1 \times 10^6$ cells/mL was prepared for expression of one type of antibody. Plasmid (200 µg in total) (i.e., an antibody heavy chain expression vector (100 µg) and an antibody light chain expression vector (100 µg)) was suspended in OPTIPRO™-SFM (is a serum-free, animal origin-free culture medium, with a very low protein concentration (<10 µg/ml). The media contains Hypoxanthine, Thymidine, Sodium Pyruvate, Sodium Bicarbonate, and Phenol Red. Thus, solution I was prepared. Next, an MAX reagent (200 µL) was added to OPTIPRO™-SFM Sodium Bicarbonate, and Phenol Red. The media is supplemented with 4 mM L-glutamine) (8 mL) (solution II). Solutions I and II were mixed and allowed to stand for 10 minutes to 20 minutes at room temperature. The reaction mixture (16 mL in total) was added to a 293 expression medium (400 mL) in which 293-F™ cells (The 293 cell line is a permanent line established from primary embryonal human kidney transformed with sheared human adenovirus type 5 DNA) were suspended. The cells were cultured in TAITEC BIOSHAKER™ (cell culture shaker) BR-43FL, which is a cell culture shaker, in 8% $CO_2$ at 37° C. for 6 to 7 days. Six or seven days later, the culture supernatant containing the recombinant antibodies was collected and purified as a material.

(4-3) Purification of the IgG Antibody

The above expressed IgG antibody protein contained in the culture supernatant was purified by an AB-CAPCHER EXTRA™ (ProteNova) affinity column using AKTAPRIME™. The obtained peak fraction was subjected to gel filtration using a SEPHACRYL™ S-300 AKTAPRIME™ (chromatography column of cross-linked copolymer of allyl dextran and N,N'-methylene bisacrylamide. The bead structure is spherical) column equilibrated with Dulbecco's PBS as a solvent for further purification. Quantitative determination of the purified IgG antibody protein was carried out by calculation using the absorption coefficient. The absorption coefficient of the IgG antibody was calculated using the total amino acid sequence of each antibody by ProtParam of EXPASY.

(5) Induction of LY6D Occurs at the Transcription Level and is Caused by Various DNA Damage Stresses.

Figure 3:
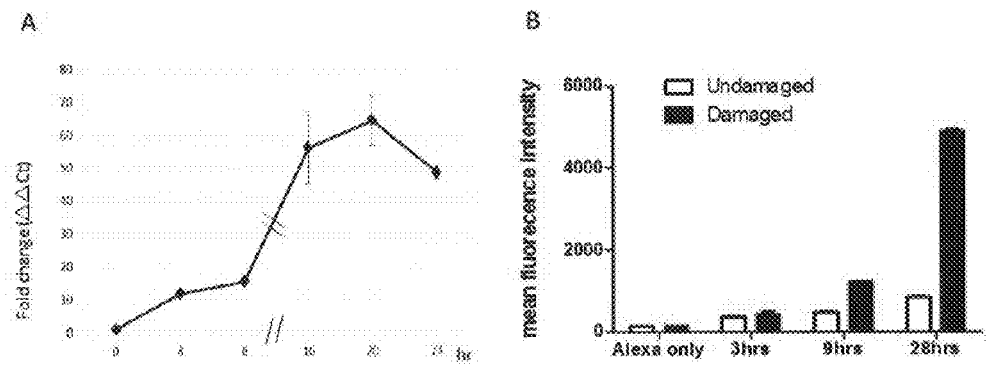
FIG. 3 shows the time course of induction of LY6D transcript and protein expression after X-ray irradiation. The amount of LY6D transcript was determined by qRT-PCR, the cycle threshold (Ct) was normalized to GADPH, and the rate of change was compared to the level of control at 0 hr (the error bar represents SEM (n=2 each)) (A: qRT-PCR (the time course of the LY6D transcript expression level after X-ray irradiation)). The amount of protein 139 was determined using a profile of FCM, and damaged MCF10A cells (black bars) and non-damaged MCF10A cells (gray bars) were incubated for an instructed period and subjected to FCM using the E33-139 monoclonal antibody (the error bar represents SEM (n=3 each)) (B: FCM (time-dependent increase of the abundance of protein 139 after X-ray irradiation)).

The time course of LY6D expression after X-ray irradiation was examined at both of the transcription level and the protein level. The amount of LY6D transcript was determined using qRT-PCR, and the amount of LY6D protein was determined using FCM. As shown in FIG. 3A, the transcription level gradually increased after irradiation and reached a plateau at about 20 hours after irradiation. The expression at the protein level of LY6D on the cell surface followed a pattern similar to that of the transcript (FIG. 3B). These results indicated that the induction of LY6D is regulated at the transcriptional level.

Figure 4:
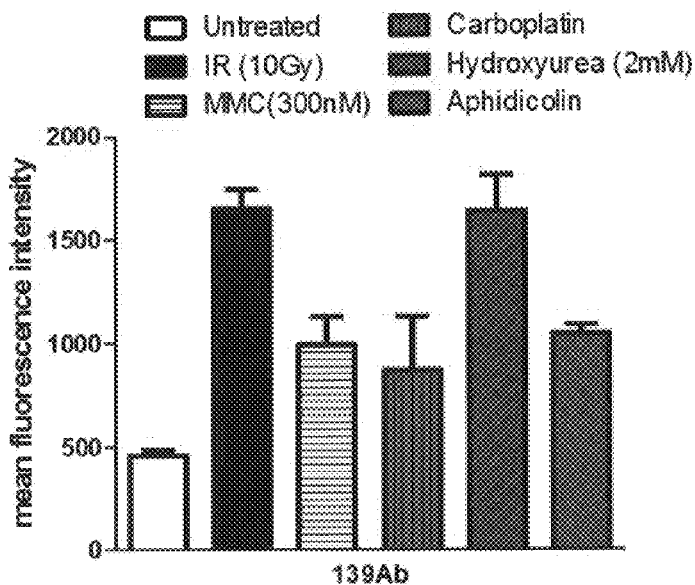
FIG. 4 shows that induction of Ly6D expression is caused by DNA damage stress. MCF10A cells were incubated with DNA-damaging stressor (MMC: 300 nM), carboplatin, hydroxyurea (2 mM), or aphidicolin and relative LY6D expression was determined by FCM.

It is well known that X-ray irradiation causes damage to DNA, which results in DNA double-strand breaks. A variety of chemical reagents also cause DNA damage stress in cells. Therefore, the influence of camptothecin (CPT) on the LY6D expression in MCF10A cells was examined. The LY6D expression on the surfaces of MCF10A cells was also induced by bringing MCF10A cells in contact with mitomycin C (MMC), carboplatin, hydroxyurea, and aphidicolin (FIG. 4). Therefore, the induction of LY6D expression on the surfaces of MCF10A cells was confirmed to be a common phenomenon due to DNA damage stress.

Figure 5:
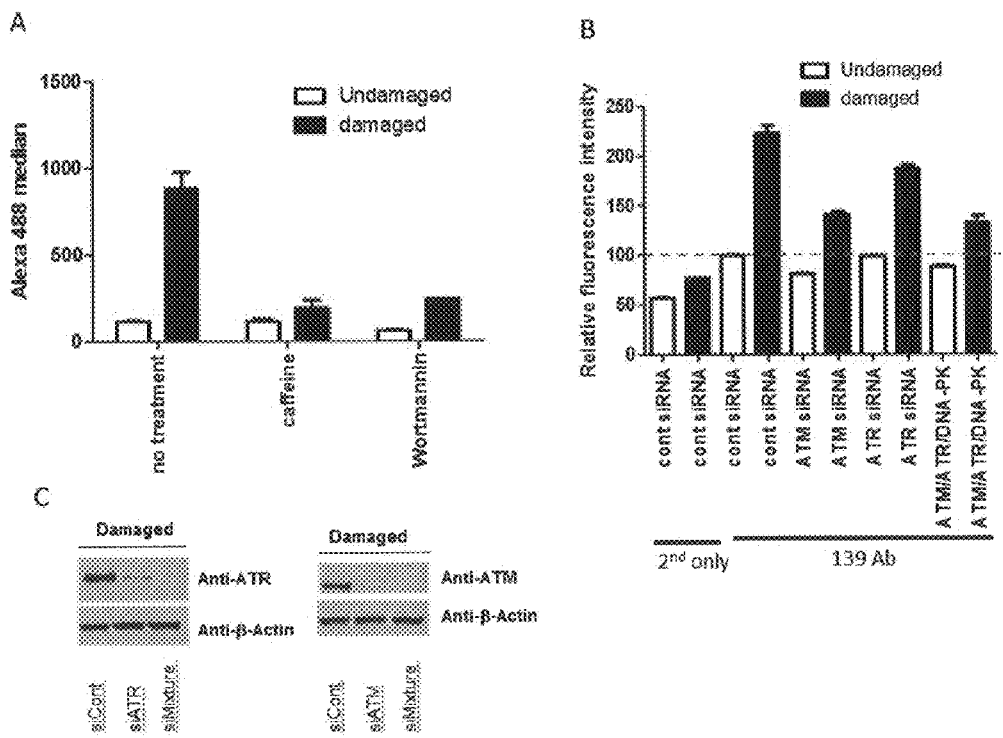
FIG. 5 shows that Ly6D expression is mediated by the ATM/ATR pathway. It is shown that LY6D expression is inhibited by an ATM/ATR inhibitor. MCF10A cells were incubated with caffeine (1 mM) or wortmannin and (1 μM) before X-ray irradiation and then the cells were X-ray irradiated and further incubated for 24 hours to determine relative LY6D expression by FCM (the error bar represents SEM (n=3 each)) (A: FCM). It is shown that LY6D expression is inhibited by ATM/ATR siRNA. MCF10A cells were treated with a mixture of ATM siRNA (25 nM), ATR siRNA (25 nM), and ATM/ATR/DNA-PK siRNA (8.3 nM each) before X-ray irradiation, relative LY6D expression was determined by FCM, and the fluorescence intensity was normalized to that of the control siRNA immunostained with 139Ab (B: FCM). Samples obtained in the experiment described in B above were subjected to western blot and immunostained with anti-ATM/ATR Ab, following which ATM and ATR proteins disappeared as a result of cell transfection by ATM siRNA and ATR siRNA, indicating that siRNA functions as expected (C: western blot).

(6) Transcription of LY6D is Caused by ATM/ATR-Mediated DNA Double-Strand Break Response To elucidate the pathway that leads to induction of LY6D expression, a chemical inhibitor was used. As shown in FIG. 5A, the elevated expression level of LY6D induced by irradiation was sensitive to caffeine, which is a PI3 kinase inhibitor such as ATM or ATR (Sarkaria et al., 1999, *Cancer Res.* 59: 4375-4382). The same phenomenon was observed for wortmannin, which is another PI3 kinase inhibitor (Powis et al., 1994, *Cancer Res.* 54: 2419-2423). An experiment using siRNA were conducted to further investigate the involvement of TM and/or ATR. The expression of LY6D induced by X-ray irradiation significantly decreased after administration of ATM siRNA to cells while it was found to slightly decrease after transfection of ATR siRNA (FIGS. 5B and 5C). These results showed that induction of LY6D expression after X-ray irradiation is brought about by signal transduction associated with DNA damage caused by ATM/ATR-mediated DNA double-strand break response, and that ATM can play a greater role than ATR in this response.

Figure 6:
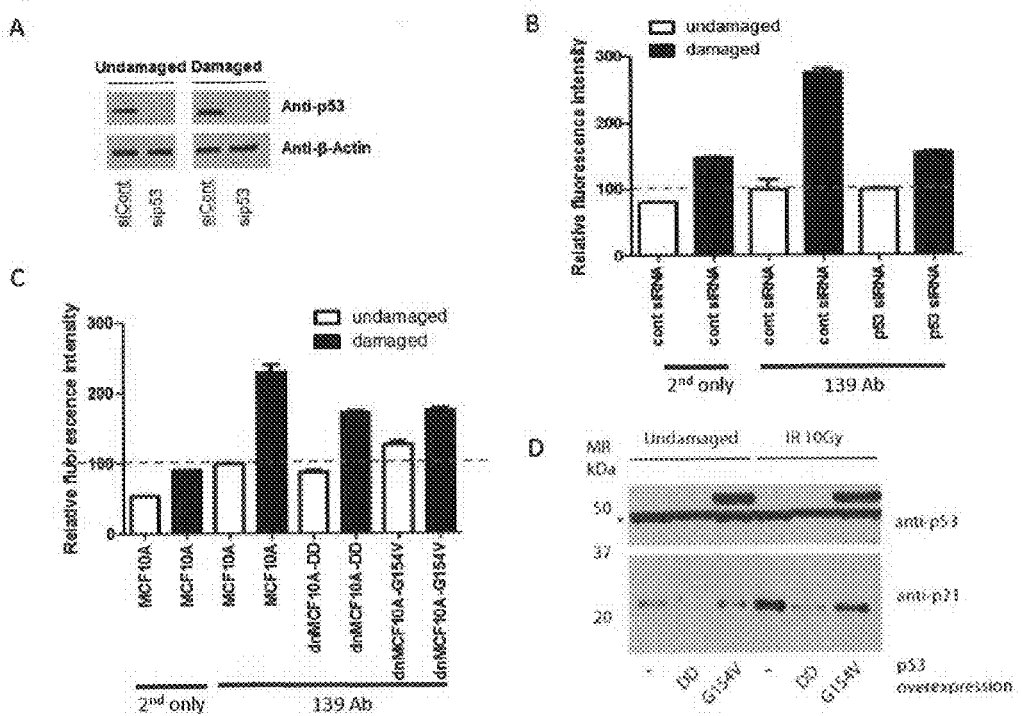
FIG. 6 shows that the p53 pathway is involved in LY6D expression. p53 siRNA (25 nM) inhibited the expression of p53 (A: western blot). Cells were treated with p53 siRNA (25 nM) and control siRNA (25 nM) before X-ray irradiation, relative LY6D expression was determined using FCM, and the fluorescence intensity was normalized to that of the non-irradiated cells treated with control siRNA and immunostained with 139Ab (the error bar represents SEM (n=3 each)) (B: FCM). LY6D expression was reduced in p53 dominant-negative MCF10A cells. Non-irradiated (white) and X-ray-irradiated (black) p53 dominant-negative MCF10A cells (TP53DD) and trans-dominant inhibition mutant cells (TP53$^{G154v}$) were subjected to FCM, and the fluorescence intensity was normalized to that of non-irradiated wild-type MCF10A cells immunostained with 139Ab (C: FCM). p53 dominant-negative MCF10A cells (TP53DD) and trans-dominant inhibition mutant cells (TP53$^{G154v}$) were subjected to western blot. Induction of p21 expression was successfully inhibited in the dominant-negative cells; however, p21 expression was observed in wild-type MCF10A cells (D: western blot).

(7) The p53-p21 Pathway is Involved in the Expression of LY6D Induced by X-Ray Irradiation Since, it has been established that ATM is activated rapidly in response to DNA double-strand breaks caused by radiation, the above experimental results are reasonable (Shiloh, 2006, *Trend. Biochem. Sci.* 31: 402-410). After being activated, ATM phosphorylates and activates various substrates. Each substrate is an important factor in the damage response pathway. The involvement of p53 was examined using siRNA (Sengupta and Harris, 2005, *Nature Cell Biol.* 6: 44-55). As shown in FIG. 6A, p53 was present in an equal amount in MCF10A cells before and after X-ray irradiation; however, transfection of the cells with p53 siRNA resulted in a significant reduction in the induction of LY6D expression after X-ray irradiation (FIG. 6B).

The involvement of p53 was also examined in MCF10A cells having a dominant-negative mutant of p53 (TP53DD: Addgene plasmid 9058) and MCF10A cells having a trans-dominant inhibition mutant $TP53^{G154V}$. As shown in FIG. 6C, induction of LY6D expression by X-ray irradiation was significantly reduced in both MCF10A cells having TP53DD and MCF10A cells having $TP53^{G154V}$. Induction of p21 expression by X-ray irradiation was observed in MCF10A having a wild type TP53; however, the degree of induction was significantly reduced in MCF10A cells having TP53DD and MCF10A cells having $TP53^{G154V}$ (FIG. 6D). These results demonstrate that the p53-p21 pathway is involved in the expression of LY6D induced by X-ray irradiation.

(8) Expression of LY6D is Induced by the Pathway Controlled by ATM, CHK2, and p53

Figure 7:
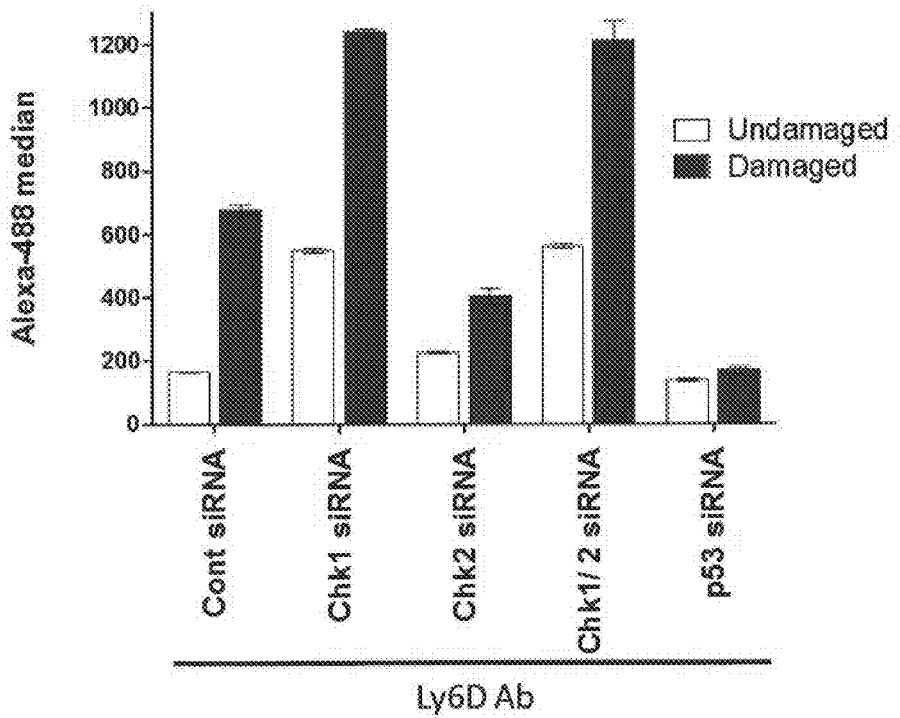
FIG. 7 shows that Chk2 siRNA inhibited LY6D expression. MCF10A cells were treated with Chk1 (25 nM), Chk2 (25 nM), or Chk1/2 (12.5 nM each) siRNA before X-ray irradiation and p53 siRNA (25 nM) was used as a control (the error bar represents SEM (n=3 each)) (FCM).

Factors such as checkpoint kinase (Bartek and Lukas, 2003, *Cancer Cell.* 3: 421-429) other than ATM and p53 may be involved in the signal transduction pathway that leads to expression of LY6D after DNA damage. As shown in FIG. 7, transfection of MCF10A cells by Chk2 siRNA significantly inhibited the induction of LY6D expression after X-ray irradiation. Thus, it was shown that induction of LY6D expression after X-ray irradiation is mediated by the route regulated by ATM, CHK2, and p53. Meanwhile, LY6D expression after X-ray irradiation could not be inhibited by Chk1 siRNA. The LY6D expression was induced by Chk1 siRNA and the degree of expression was significantly increased as a result of X-ray irradiation (FIG. 7). These results probably reflect the fact that Chk1 is not directly involved in induction of LY6D expression after X-ray irradiation; however, inhibition of Chk1 causes DNA damage (Syljuasen et al., 2005, *Mol. Cell. Biol.* 25: 3553-3562).

Figure 8:
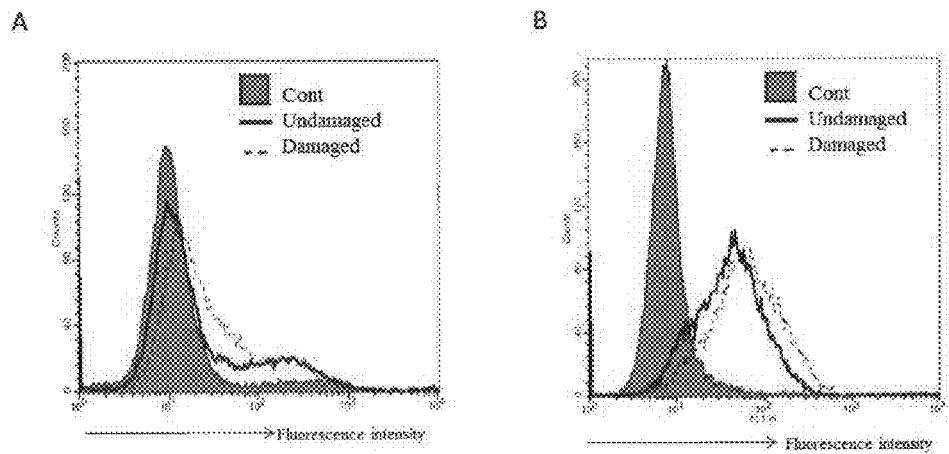
FIG. 8 shows LY6D expression in FaDu and A431 cells. FaDu cells were treated by X-ray irradiation and then FCM analysis was conducted using the E33-139 monoclonal antibody (black line: non-damaged cells having the E33-139 monoclonal antibody; dashed line: non-damaged cells having the E33-139 monoclonal antibody; and grey: non-damaged cells not having the E33-139 monoclonal antibody) (A: FCM). A431 cells were treated by X-ray irradiation and then subjected to FCM analysis using the E33-139 monoclonal antibody (black line: non-damaged cells having the E33-139 monoclonal antibody; dashed line: non-damaged cells having the E33-139 monoclonal antibody; and grey: non-damaged cells not having the E33-139 monoclonal antibody) (B: FCM).

(9) LY6D Expression in FaDu and A431 Cells is Further Enhanced by X-Ray Irradiation LY6D was originally identified as an antigen recognized by the E48 monoclonal antibody isolated after immunization of mice with HNSCC cells (Quak et al., 1990, *Am J. Pathol.* 136: 191-197). As a result of examination of the LY6D expression in 12 cancer cell lines that had not been exposed to X-ray irradiation, only the two cell lines, i.e., FaDu and A431, were found to have expressed LY6D. Next, the effects of X-ray irradiation on the LY6D expression in these cell lines were examined. After X-ray irradiation, the LY6D expression in FaDu and A431 cells was further enhanced (FIG. 8). Further, the LY6D expression in two cell lines derived from normal tissue, i.e., the human mammalian epithelial cell line (HMEC) and the retinal pigment epithelial cell line (RPE) was also examined. It was found that LY6D is not expressed in any of these cell lines under normal culture conditions or depending on X-ray irradiation. Accordingly, the induction of the LY6D expression by X-ray irradiation is considered to be a phenomenon of cells under some specific conditions which have not yet been identified.

DISCUSSION ON THE EXAMPLES

In the Examples, a method for identifying a membrane protein expressed depending on X-ray irradiation was developed. This method can be applied to the analysis of other biological phenomena on a situation in which both of cells that express a target molecule and cells that do not express a target molecule can be used. Candidate antibody clones can be selected using this method. In order to promote the selection of isolated clones, it is desirable that the difference between two cell populations be limited to the presence/absence of target molecule(s). In this case, desired clones can be easily determined using cell ELISA.

By using the method developed by the present inventors, it was found that expression of the membrane protein LY6D on the surfaces of MCF10A cells is induced by X-ray irradiation. This phenomenon was observed mainly in this cell line among a small number of previously studied cell lines derived from normal tissue. The data of the Examples show that induction of expression of the membrane protein LY6D on the surfaces of MCF10A cells is a common phenomenon caused by DNA damage stress. DNA damage gives some effects such as cell cycle arrest, increased DNA repair function, and apoptosis on cells (Zhou and Elledge, 2000, *Nature* 408: 433-439). The major factors involved in such responses are located in the nucleus or cytoplasm but not the cell membrane. NKG2D ligand is a membrane protein that is known to be induced by DNA damage. Elevation in the expression level of NKG2D ligand is initiated by ATM and/or ATR and mediated by the major DNA damage response pathway inherited to downstream mediating factors CHK1 and CHK2. (Gasser et al., 2005, *Nature* 436: 1186-1190). However, p53 is not necessary for elevation of the expression level of NKG2D ligand (Gasser et al., 2005, *Nature* 436: 1186-1190). In contrast, induction of LY6D expression is regulated by ATM, CHK2, and p53.

The LY6D gene belongs to the Ly6 gene family. Mouse Ly-6 was originally identified as a surface glycoprotein expressed in a specific leukocyte subpopulation of peripheral lymphoid tissue during hematopoiesis in pluripotent stem cells and the precursor cells exclusive for the lineage (Gumley et al., 1995, *Cell Biol.* 73: 277-296). Mouse Ly-6 also known as ThB is expressed in all mature B cells and plasmacytoid dendritic cells and immature lymphocytes of the thymus at the developing stage (Gumley et al., 1992, *J. Immunol.* 149: 2615-2618; and Inlay et al., 2009, *Gene Develop.* 23: 2376-2381). However, human LY6D which is considered to be a homolog of mouse Ly6d is not expressed in lymphocytes (Brakenhoff et al., 1995, *J. Cell Biol.* 129: 1677-1689; and Quak et al., 1990, *Am J. Pathol.* 136: 191-197), suggesting that human LY6D and mouse Ly6d have evolved differently (Brakenhoff et al., 1997, *J. Immunol.* 159: 4879-4886).

Figure 9:
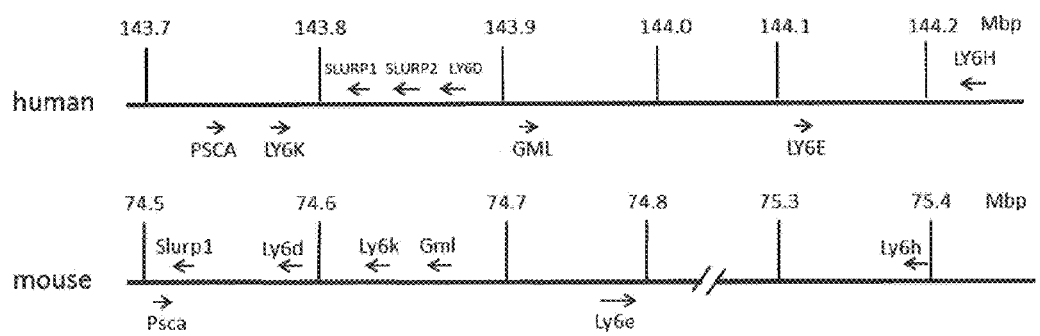
FIG. 9 shows a comparison of gene organization of the LY6 family gene between the human chromosome 8q24.3 and the mouse chromosome 15. In humans, eight LY6 family genes are concentrated on chromosome 8q24.3. In mice, thirteen LY6 family genes are concentrated on the chromosome 15. The directions of genes encoded by genome DNA are indicated by arrows.

Many of the genes encoding the Ly6 family members are located in chromosome 8q24.3 in humans and the chromosome 15 in mice (De Nooij-van Dalen et al., 2003, *Int. J. Cancer* 103, 768-774; And Stroncek et al., 2004, *J. Translat. Med.* 2: 1-9). FIG. 9 shows a schematic comparison in terms of the gene organization of the Ly6 gene region between the human chromosome and the mouse chromosome. In the figure, eight human LY6 family genes and thirteen mouse Ly6 family genes are mapped to their regions. Among these genes, 7 homologues, i.e., LY6D, LY6E, LY6H, LY6K, GML, PSCA, and SLURP1, have been identified in both the human genome and the mouse genome. The PSCA, LY6E, and LY6H genes are located in important positions of the human genome and the mouse genome. The six Ly6 family genes gather between the LY6E gene locus and the LY6H gene locus of the mouse genome, while none of these genes exists in the human genome. Meanwhile, five human genes and four mouse genes are located between the PSCA gene locus and the LY6E gene locus, and they are organized differently in the human genome and the mouse genome.

The expression of the human GML gene is induced specifically by p53 (Furuhata et al., 1996, *Oncogene.* 13: 1965-1970). In the human genome, the LY6D and GML genes are adjacent to each other in a configuration in which they are arranged in a head-to-head order. The p53 binding sequence is positioned at a position away from the 5' flanking region of GML by a distance of 19 kb (El-Deiry et al., 1992, *Nature Genet.* 1: 45-49; and Kimura et al., 1997, *Genomics.* 41: 477-480). The position corresponds to the 5' flanking region of LY6D away from LY6D by a distance of 27 kb. Mouse Ly6d and Gml are not oriented in the head-to-head configuration. Moreover, Ly6k is embedded between the Ly6d gene locus and the Gml gene locus of the mouse genome. Mouse Gml also known as HemT-3 was identified in a manner completely different from that for human GML (Xue et al., 1999, *Gene.* 240: 193-199). HemT is preferentially expressed in mouse erythroleukemia cells and three types of HemT transcripts, i.e., HemT-1, HemT-2, and HemT-3m, were identified. The amino acid sequence of HemT-3 has a high degree of identity to that of GML and thus the genes are considered homologous to each other. Accordingly, it is considered that human LY6D and GML have developed functions different from those of mouse Ly6d and Gml so that human LY6D and GML have become to be regulated by p53.

It was reported that the LY6D expression is significantly enhanced by chemotherapy treatment with a topoisomerase inhibitor, i.e., irinotecan (Rubinfeld et al., 2006, *Nature Biotech.* 24: 205-209). If this phenomenon would be associated with the results of this Example, induction of LY6D expression may be associated with acquired resistance to DNA damage. Interestingly, a correlation between the presence of GML expression and the sensitivity of cancer cells to anti-cancer drugs such as taxol and cisplatin was observed (Furuhata et al., 1996, *Oncogene.* 13: 1965-1970; Kimura et al., 1997, *Oncogene.* 15: 1369-1374; and Higashiyama et al., 2000, *Eur J. Cancer.* 36: 489-495). LY6D and GML seem to function in an opposite manner in response to DNA damage. The p53 binding site in the 46-kb region between the GML gene and the LY6D gene was searched for using p53 scanning. As a result, only one consensus binding site of p53 was found in this region. Therefore, the both genes are likely to be regulated under the same p53 binding site. However, as a result of analysis using qRT-PCR and FCM, the expression of GML in MCF1OA cells is not induced by X-ray irradiation. Accordingly, in addition to p53, there should be several factors for dominating the expression of either LY6D or GML.

The invention claimed is:

1. An antibody that specifically reacts with human Ly6D having: a heavy chain variable region comprising a heavy chain first complementarity-determining region (VH CDR1) comprising the sequence of SEQ ID NO: 3, a heavy chain second complementarity-determining region (VH CDR2) comprising the sequence of SEQ ID NO: 4, and a heavy chain third complementarity-determining region (VH CDR3) comprising the sequence of SEQ ID NO: 5; and a light chain variable region comprising a light chain first complementarity-determining region (VL CDR1) comprising the sequence of SEQ ID NO: 6, a light chain second complementarity-determining region (VL CDR2) comprising the sequence of SEQ ID NO: 7, and a light chain third complementarity-determining region (VL CDR3) comprising the sequence of SEQ ID NO: 8.

2. The antibody of claim 1, wherein the antibody is a human antibody.

3. The antibody of claim 1, wherein the antibody is an antibody fragment selected from the group consisting of Fab, Fab', F(ab')$_2$, scFv, Diabody, and dsFv.

4. An isolated DNA encoding the antibody of claim 1.

5. An isolated recombinant vector which comprises the isolated DNA of claim 4.

6. An isolated transformant obtained by introducing the isolated recombinant vector of claim 5 into an isolated host cell.

7. A reagent for detecting DNA damage comprising the antibody of claim 1.

8. A pharmaceutical composition comprising the antibody of claim 1.

9. The pharmaceutical composition of claim 8, further comprising a cytotoxic substance that is bound to the antibody.

10. The pharmaceutical composition of claim 9, wherein the cytotoxic substance is a drug, toxin, or radioactive substance.

11. The pharmaceutical composition of claim 8, wherein the antibody detects DNA damage in cells.

12. The pharmaceutical composition of claim 8, wherein the antibody detects cancer which expresses LY6D protein.

* * * * *

SEQUENCE LISTING

<160> NUMBER OF SEQ ID NOS: 39

<210> SEQ ID NO 1
<211> LENGTH: 1065
<212> TYPE: DNA
<213> ORGANISM: human
<220> FEATURE:
<221> NAME/KEY: CDS
<222> LOCATION: (1)..(1065)

<400> SEQUENCE: 1

```
atg gcc gag gtg cag ctg gtg gag tct ggg gga ggc ttg gta cag cct        48
Met Ala Glu Val Gln Leu Val Glu Ser Gly Gly Gly Leu Val Gln Pro
1               5                   10                  15 ggc agg tcc ctg aga ctc tcc tgt gca gcc tct gga ttc acc ttt gat        96
Gly Arg Ser Leu Arg Leu Ser Cys Ala Ala Ser Gly Phe Thr Phe Asp
            20                  25                  30 gat tat gcc atg cac tgg gtc cgg caa gct cca ggg aag ggc ctg gag       144
Asp Tyr Ala Met His Trp Val Arg Gln Ala Pro Gly Lys Gly Leu Glu
        35                  40                  45 tgg gtc tca ggt att agt tgg aat agt ggt agc ata ggc tat gcg gac       192
Trp Val Ser Gly Ile Ser Trp Asn Ser Gly Ser Ile Gly Tyr Ala Asp
    50                  55                  60 tct gtg aag ggc cga ttc acc atc tcc aga gac aac gcc aag aac tcc       240
Ser Val Lys Gly Arg Phe Thr Ile Ser Arg Asp Asn Ala Lys Asn Ser
65                  70                  75                  80 ctg tat ctg caa atg aac agt ctg aga gct gag gac acg gcc ttg tat       288
Leu Tyr Leu Gln Met Asn Ser Leu Arg Ala Glu Asp Thr Ala Leu Tyr
                85                  90                  95 tac tgt gca aaa acg ggg atc ctc gat gct ttt gat atc tgg ggc caa       336
Tyr Cys Ala Lys Thr Gly Ile Leu Asp Ala Phe Asp Ile Trp Gly Gln
            100                 105                 110 ggg acc acg gtc acc gtc tcg aga ggc ggt ggc gga tca ggt ggc ggt       384
Gly Thr Thr Val Thr Val Ser Arg Gly Gly Gly Gly Ser Gly Gly Gly
        115                 120                 125 gga agt ggc ggt ggt ggg tcc atg gcc cag tct gtg ttg acg cag ccg       432
Gly Ser Gly Gly Gly Gly Ser Met Ala Gln Ser Val Leu Thr Gln Pro
    130                 135                 140 ccc tcg gtg tct ggg gcc ccc cgg cag acg gtc acc atc tcc tgc tct       480
Pro Ser Val Ser Gly Ala Pro Arg Gln Thr Val Thr Ile Ser Cys Ser
145                 150                 155                 160 ggg agc agc tcc aac atc gga caa aat tct gtt acc tgg tac cag cgc       528
Gly Ser Ser Ser Asn Ile Gly Gln Asn Ser Val Thr Trp Tyr Gln Arg
                165                 170                 175 ctc ccg ggt gag gct ccc aaa ctc ctc atc tac tat gat gat ctc ttg       576
Leu Pro Gly Glu Ala Pro Lys Leu Leu Ile Tyr Tyr Asp Asp Leu Leu
            180                 185                 190 cac tca gga gtc tct gac cga ttc tct ggc tcc aag tct ggc acc tca       624
His Ser Gly Val Ser Asp Arg Phe Ser Gly Ser Lys Ser Gly Thr Ser
        195                 200                 205 gcc tca ctg gcc atc agt gga ctc cag tct gag gat gag gct gag tac       672
Ala Ser Leu Ala Ile Ser Gly Leu Gln Ser Glu Asp Glu Ala Glu Tyr
    210                 215                 220 tac tgt gcg tca tgg gat gac agc ctg aaa ggt ccg gta ttc ggc gga       720
Tyr Cys Ala Ser Trp Asp Asp Ser Leu Lys Gly Pro Val Phe Gly Gly
225                 230                 235                 240
```

```
ggg acc aaa ctg acc gtc cta ggt cag ccc aag gct gcc ccc tcg gtc      768
Gly Thr Lys Leu Thr Val Leu Gly Gln Pro Lys Ala Ala Pro Ser Val
                245                 250                 255 act ctg ttc ccg ccc tcc tct gag gag ctt caa gcc aac aag gcc aca      816
Thr Leu Phe Pro Pro Ser Ser Glu Glu Leu Gln Ala Asn Lys Ala Thr
                260                 265                 270 ctg gtg tgt ctc ata agt gac ttc tac ccg gga gcc gtg aca gtg gcc      864
Leu Val Cys Leu Ile Ser Asp Phe Tyr Pro Gly Ala Val Thr Val Ala
                275                 280                 285 tgg aag gca gat agc agc ccc gtc aag gcg gga gtg gag acc acc aca      912
Trp Lys Ala Asp Ser Ser Pro Val Lys Ala Gly Val Glu Thr Thr Thr
                290                 295                 300 ccc tcc aaa caa agc aac aac aag tac gcg gcc agc agc tac ctg agc      960
Pro Ser Lys Gln Ser Asn Asn Lys Tyr Ala Ala Ser Ser Tyr Leu Ser
305                 310                 315                 320 ctg acg cct gag cag tgg aag tcc cac aaa agc tac agc tgc cag gtc     1008
Leu Thr Pro Glu Gln Trp Lys Ser His Lys Ser Tyr Ser Cys Gln Val
                325                 330                 335 acg cat gaa ggg agc acc gtg gag aag aca gtg gcc cct aca gaa tgt     1056
Thr His Glu Gly Ser Thr Val Glu Lys Thr Val Ala Pro Thr Glu Cys
                340                 345                 350 tcg gcg cgc                                                         1065
Ser Ala Arg
355

<210> SEQ ID NO 2
<211> LENGTH: 355
<212> TYPE: PRT
<213> ORGANISM: human

<400> SEQUENCE: 2

Met Ala Glu Val Gln Leu Val Glu Ser Gly Gly Gly Leu Val Gln Pro
1               5                   10                  15

Gly Arg Ser Leu Arg Leu Ser Cys Ala Ala Ser Gly Phe Thr Phe Asp
                20                  25                  30

Asp Tyr Ala Met His Trp Val Arg Gln Ala Pro Gly Lys Gly Leu Glu
            35                  40                  45

Trp Val Ser Gly Ile Ser Trp Asn Ser Gly Ser Ile Gly Tyr Ala Asp
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Leu Tyr
                85                  90                  95

Tyr Cys Ala Lys Thr Gly Ile Leu Asp Ala Phe Asp Ile Trp Gly Gln
                100                 105                 110

Gly Thr Thr Val Thr Val Ser Arg Gly Gly Gly Gly Ser Gly Gly Gly
            115                 120                 125

Gly Ser Gly Gly Gly Ser Met Ala Gln Ser Val Leu Thr Gln Pro
        130                 135                 140

Pro Ser Val Ser Gly Ala Pro Arg Gln Thr Val Thr Ile Ser Cys Ser
145                 150                 155                 160

Gly Ser Ser Ser Asn Ile Gly Gln Asn Ser Val Thr Trp Tyr Gln Arg
                165                 170                 175

Leu Pro Gly Glu Ala Pro Lys Leu Leu Ile Tyr Tyr Asp Asp Leu Leu
            180                 185                 190

His Ser Gly Val Ser Asp Arg Phe Ser Gly Ser Lys Ser Gly Thr Ser
        195                 200                 205
```

```
            Ala Ser Leu Ala Ile Ser Gly Leu Gln Ser Glu Asp Glu Ala Glu Tyr
                210                 215                 220

Tyr Cys Ala Ser Trp Asp Asp Ser Leu Lys Gly Pro Val Phe Gly Gly
            225                 230                 235                 240

Gly Thr Lys Leu Thr Val Leu Gly Gln Pro Lys Ala Ala Pro Ser Val
                            245                 250                 255

Thr Leu Phe Pro Pro Ser Ser Glu Glu Leu Gln Ala Asn Lys Ala Thr
                        260                 265                 270

Leu Val Cys Leu Ile Ser Asp Phe Tyr Pro Gly Ala Val Thr Val Ala
                    275                 280                 285

Trp Lys Ala Asp Ser Ser Pro Val Lys Ala Gly Val Glu Thr Thr Thr
                290                 295                 300

Pro Ser Lys Gln Ser Asn Asn Lys Tyr Ala Ala Ser Ser Tyr Leu Ser
            305                 310                 315                 320

Leu Thr Pro Glu Gln Trp Lys Ser His Lys Ser Tyr Ser Cys Gln Val
                            325                 330                 335

Thr His Glu Gly Ser Thr Val Glu Lys Thr Val Ala Pro Thr Glu Cys
                        340                 345                 350

Ser Ala Arg
                    355

<210> SEQ ID NO 3
<211> LENGTH: 5
<212> TYPE: PRT
<213> ORGANISM: human

<400> SEQUENCE: 3

Asp Tyr Ala Met His
1               5

<210> SEQ ID NO 4
<211> LENGTH: 17
<212> TYPE: PRT
<213> ORGANISM: human

<400> SEQUENCE: 4

Gly Ile Ser Trp Asn Ser Gly Ser Ile Gly Tyr Ala Asp Ser Val Lys
1               5                   10                  15

Gly

<210> SEQ ID NO 5
<211> LENGTH: 9
<212> TYPE: PRT
<213> ORGANISM: human

<400> SEQUENCE: 5

Thr Gly Ile Leu Asp Ala Phe Asp Ile
1               5

<210> SEQ ID NO 6
<211> LENGTH: 13
<212> TYPE: PRT
<213> ORGANISM: human

<400> SEQUENCE: 6

Ser Gly Ser Ser Ser Asn Ile Gly Gln Asn Ser Val Thr
1               5                   10
```

```
<210> SEQ ID NO 7
<211> LENGTH: 7
<212> TYPE: PRT
<213> ORGANISM: human

<400> SEQUENCE: 7

Tyr Asp Asp Leu Leu His Ser
1               5

<210> SEQ ID NO 8
<211> LENGTH: 11
<212> TYPE: PRT
<213> ORGANISM: human

<400> SEQUENCE: 8

Ala Ser Trp Asp Asp Ser Leu Lys Gly Pro Val
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: linker

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 118
<212> TYPE: PRT
<213> ORGANISM: human

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Thr Gly Ile Leu Asp Ala Phe Asp Ile Trp Gly Gln Gly Thr
            100                 105                 110

Thr Val Thr Val Ser Ser
        115

<210> SEQ ID NO 11
<211> LENGTH: 330
<212> TYPE: PRT
<213> ORGANISM: human

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 110
<212> TYPE: PRT
<213> ORGANISM: human

<400> SEQUENCE: 12

Gln Ser Val Leu Thr Gln Pro Pro Ser Val Ser Gly Ala Pro Arg Gln
1               5                   10                  15

Thr Val Thr Ile Ser Cys Ser Gly Ser Ser Ser Asn Ile Gly Gln Asn
            20                  25                  30

Ser Val Thr Trp Tyr Gln Arg Leu Pro Gly Glu Ala Pro Lys Leu Leu
        35                  40                  45

Ile Tyr Tyr Asp Asp Leu Leu His Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80
```

```
Ser Glu Asp Glu Ala Glu Tyr Tyr Cys Ala Ser Trp Asp Asp Ser Leu
                85                  90                  95
Lys Gly Pro Val Phe Gly Gly Thr Lys Leu Thr Val Leu
            100                 105                 110

<210> SEQ ID NO 13
<211> LENGTH: 106
<212> TYPE: PRT
<213> ORGANISM: human

<400> SEQUENCE: 13

Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30
Phe Tyr Pro Gly Ala Val Thr Val Ala Trp Lys Ala Asp Ser Ser Pro
        35                  40                  45
Val Lys Ala Gly Val Glu Thr Thr Thr Pro Ser Lys Gln Ser Asn Asn
    50                  55                  60
Lys Tyr Ala Ala Ser Ser Tyr Leu Ser Leu Thr Pro Glu Gln Trp Lys
65                  70                  75                  80
Ser His Lys Ser Tyr Ser Cys Gln Val Thr His Glu Gly Ser Thr Val
                85                  90                  95
Glu Lys Thr Val Ala Pro Thr Glu Cys Ser
            100                 105

<210> SEQ ID NO 14
<211> LENGTH: 25
<212> TYPE: RNA
<213> ORGANISM: Artificial Sequence
<220> FEATURE:
<223> OTHER INFORMATION: Description of Artificial Sequence: siRNA

<400> SEQUENCE: 14
uccaagucau cagcauucca ugccc                                          25

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 15
gcaaagaggu ggcaguuaa                                                 19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 16
gagcaucacu ugccuuuaa                                                 19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: siRNA
```

```
<400> SEQUENCE: 17
gaugagaagu ccuuaggua                                                    19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 18
gcaggaccgu gcaagguua                                                    19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 19
gcaaagcccu aguaacaua                                                    19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 20
gggcauuacg gguguugaa                                                    19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 21
ucgcuuagca ggaggugua                                                    19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 22
ugaugaagag agacggaau                                                    19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 23
gaacaacacu gcugguuug                                                    19
```

```
<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 24
gcaacucgcc uaacagaua                                                19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 25
ucucagaagu caaccgauu                                                19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 26
gaauuguguu gcagagcuu                                                19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 27
caagaugugu gguacuuua                                                19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 28
gagaaggcaa uauccaaua                                                19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 29
ccacaugucc ugaucauau                                                19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: siRNA
```

```
<400> SEQUENCE: 30 gaaguuggc uaucaaugg                                                    19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 31
cucaggaacu cuauucuau                                                   19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 32
guugugaacu ccgugguuu                                                   19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 33
gcauaggacu caaguguca                                                   19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 34
guaagaaagu agccauaaa                                                   19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 35
cagucuaccu cccgccaua                                                   19

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 36
agatgaggac agcattgctg c                                                21
```

```
<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 37
gcagaccaca gaatgcttgc                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 38
acttcaacag cgacacccac                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 39
caactgtgag gaggggagat                                                    20
```